US012697215B2

(12) United States Patent     (10) Patent No.: US 12,697,215 B2

Lopez et al.     (45) Date of Patent: Aug. 4, 2026

(54) LOADING ASSEMBLY AND DELIVERY APPARATUS FOR AN EXPANDABLE PROSTHETIC MEDICAL DEVICE

(71) Applicant: EDWARDS LIFESCIENCES CORPORATION, Irvine, CA (US)

(72) Inventors: Jose Luis Lopez, Cypress, CA (US); Salomon Xavier Valencia, Aliso Viejo, CA (US); Brad Buzea, Trabuco Canyon, CA (US); Alessandro Marco Leggio Yepez, Boca Raton, FL (US)

(73) Assignee: Edwards Lifesciences Corporation, Irvine, CA (US)

( * ) Notice: Subject to any disclaimer, the term of this patent is extended or adjusted under 35 U.S.C. 154(b) by 432 days.

(21) Appl. No.: 18/524,658

(22) Filed: Nov. 30, 2023

(65) Prior Publication Data

US 2024/0156596 A1     May 16, 2024

Related U.S. Application Data

(63) Continuation of application No. PCT/US2022/033287, filed on Jun. 13, 2022.

(60) Provisional application No. 63/210,421, filed on Jun. 14, 2021.

(51) Int. Cl.
*A61F 2/24* (2006.01)
*A61F 2/95* (2013.01)

(52) U.S. Cl.
CPC .......... *A61F 2/2439* (2013.01); *A61F 2/2436* (2013.01); *A61F 2/9522* (2020.05)

(58) Field of Classification Search
CPC .... A61F 2/2436; A61F 2/9522; A61F 2/2427; A61F 2/9517; A61F 2/2439; A61F 2/243; A61F 2/95
See application file for complete search history.

(56) References Cited

U.S. PATENT DOCUMENTS

| | | | |
|---|---|---|---|
| 519,297 | A | 5/1894 | Wanek et al. |
| 4,035,849 | A | 7/1977 | Angell et al. |
| 4,592,340 | A | 6/1986 | Boyles |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Katherine M Shi

(74) *Attorney, Agent, or Firm* — Klarquist Sparkman, LLP

(57) ABSTRACT

Systems and methods for securely connecting a loading assembly to a delivery apparatus for loading a prosthetic medical device into the delivery apparatus are disclosed. As one example, a medical system can include a delivery apparatus for implanting a prosthetic medical device in a patient's body and a loading system. The delivery apparatus can comprise a flexible shaft, a coupling attached to a distal end of the flexible shaft, and a delivery capsule coupled to the coupling and extending distally from the coupling. The loading assembly can comprise a loading capsule comprising a plurality of axially extending flexible members configured to couple to an outer surface of the coupling and flex radially outward and a collar disposed around the loading capsule and configured to lock the plurality of flexible members in engagement with the coupling such that the plurality of flexible members cannot flex radially outward.

10 Claims, 17 Drawing Sheets

(56)                References Cited

U.S. PATENT DOCUMENTS

| | | | |
|---|---|---|---|
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |

| | | | |
|---|---|---|---|
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 11,273,038 B2 | 3/2022 | Tang et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0103520 A1 | 5/2008 | Selkee |
| 2008/0125853 A1 | 5/2008 | Bailey et al. |
| 2008/0294230 A1 | 11/2008 | Parker |
| 2009/0024428 A1 | 1/2009 | Hudock |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |
| 2012/0330408 A1* | 12/2012 | Hillukka ............... A61F 2/2427 |
| | | 623/2.11 |
| 2013/0030519 A1 | 1/2013 | Tran et al. |
| 2013/0317598 A1 | 11/2013 | Rowe et al. |
| 2014/0296962 A1 | 10/2014 | Cartledge et al. |

(56)  References Cited

U.S. PATENT DOCUMENTS

| | | | |
|---|---|---|---|
| 2017/0065415 | A1 | 3/2017 | Rupp et al. |
| 2018/0153689 | A1 | 6/2018 | Maimon et al. |
| 2018/0344456 | A1 | 12/2018 | Barash et al. |

FOREIGN PATENT DOCUMENTS

| | | | |
|---|---|---|---|
| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

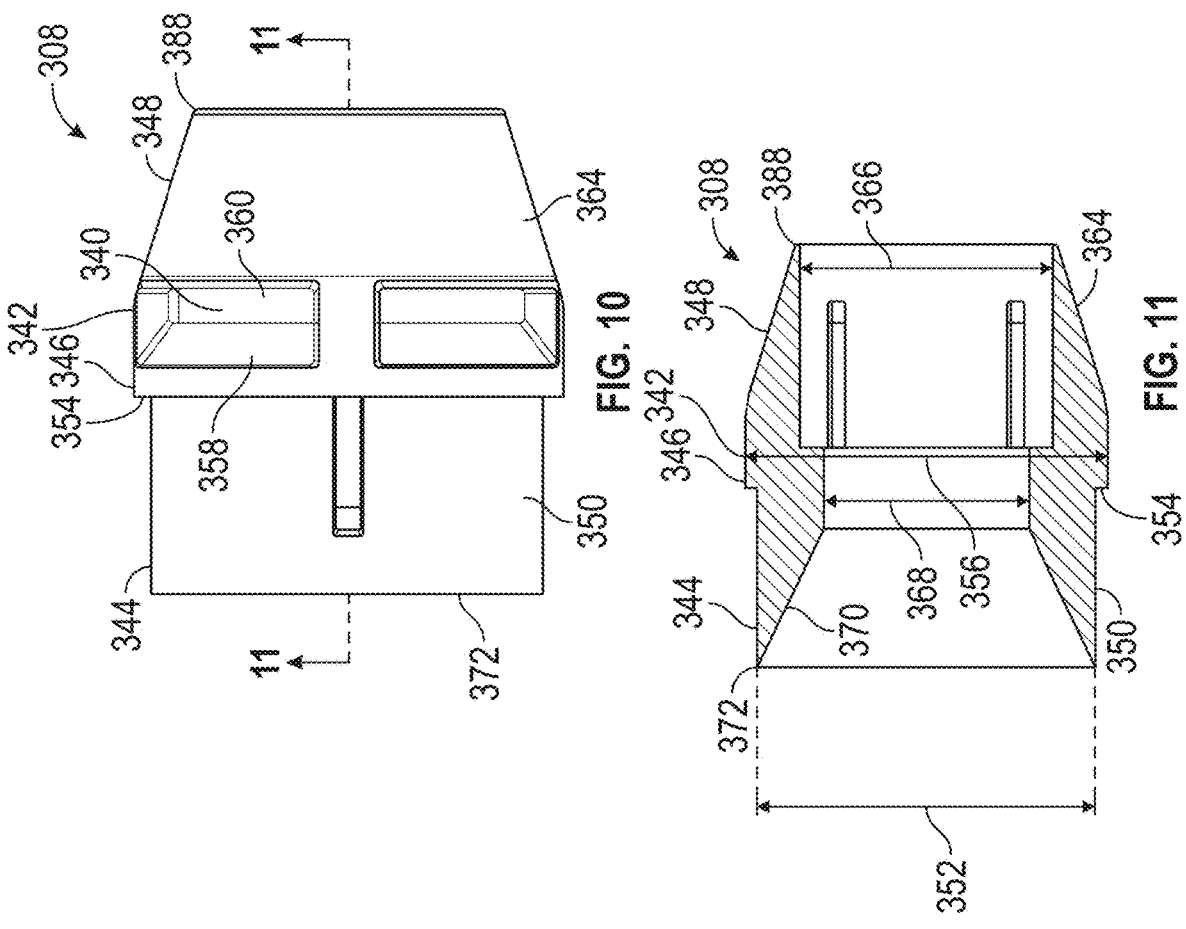
FIG. 10
FIG. 11
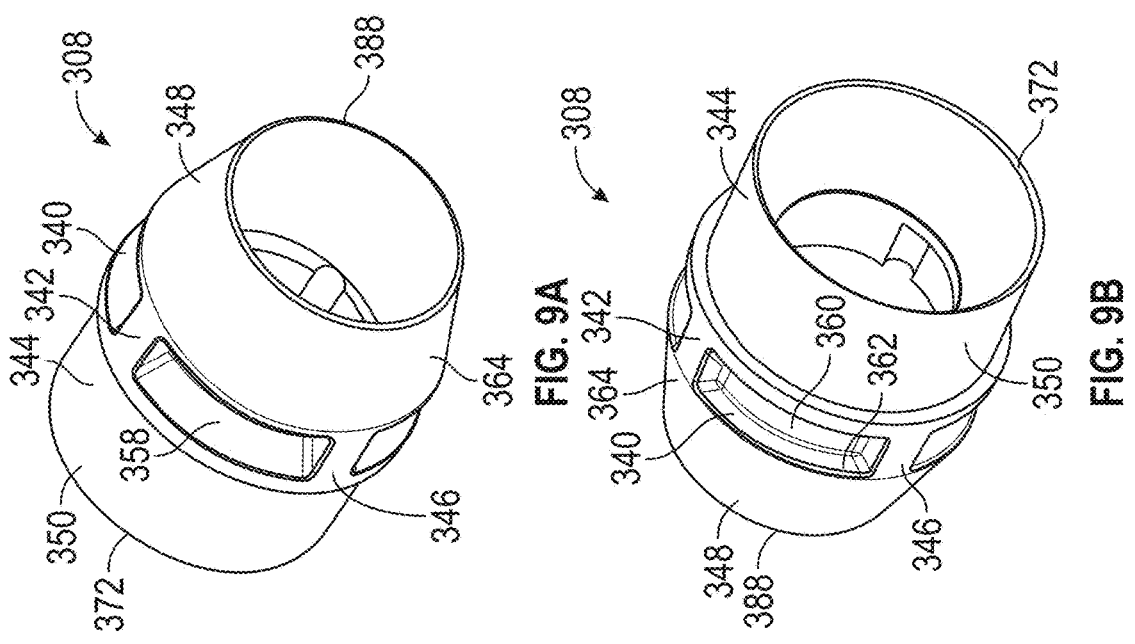
FIG. 9A
FIG. 9B

Start

╭─ 1100

1102

Arrange a loading capsule of a loading assembly around a delivery capsule of a delivery apparatus, the delivery capsule coupled to a distal end of a shaft of the delivery apparatus by a coupling

1104

Move a proximal end portion of the loading capsule comprising a plurality of axially-extending flexible members into contact with the coupling and flex the flexible members radially outward as they slide along an outer surface of the coupling

1106

Move the flexible members radially inward and into engagement with one or more channels depressed into the outer surface of the coupling, thereby coupling the loading capsule to the coupling

1108

Slide a collar of the loading assembly over the outer surface of the loading capsule, from a disengaged position to an engaged position where one or more locking features of the collar engage one or more complementary locking features on an outer surface of the flexible members and lock the flexible members in engagement with the coupling such that they cannot flex radially outward (thereby locking the loading assembly to the delivery apparatus)

1110

Attach a device housing to a distal end portion of the loading assembly and arrange the prosthetic medical device within the device housing for storage and/or transport

1112

Load a prosthetic medical device into the delivery capsule by at least partially radially compressing the prosthetic medical device and sliding it into and through a tapered loading member (loader) of the loading assembly that is coupled to a distal end portion of the loading capsule and further radially compressing the prosthetic medical device as it slides through the loading member and into the delivery capsule End

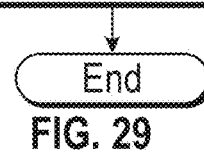

FIG. 29

LOADING ASSEMBLY AND DELIVERY APPARATUS FOR AN EXPANDABLE PROSTHETIC MEDICAL DEVICE

CROSS-REFERENCE TO RELATED APPLICATIONS

This application is a continuation of PCT Application No. PCT/US2022/033287, filed Jun. 13, 2022, which claims the benefit of U.S. Provisional Patent Application No. 63/210, 421, filed Jun. 14, 2021, each of which is incorporated by reference herein in its entirety.

FIELD

The present disclosure relates to a loading assembly for loading a prosthetic medical device into a delivery apparatus.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart.

Once at the implantation site, the prosthetic heart valve can be expanded to its functional size by, for example, actuating a mechanical actuator that applies a radially outward force to the prosthetic valve. Such prosthetic heart valves (ones that rely on a mechanical actuator for expansion) can be referred to as "mechanically expandable" prosthetic heart valves.

In other examples, the prosthetic heart valve can be self-expanding. For example, such self-expanding valves can be constructed from a shape-memory material and can be pre-formed in a radially expanded state so that the prosthetic valves are naturally biased to this radially expanded state. Such self-expanding valves can be held in a crimped state by a restraint (e.g., a sheath or capsule) during delivery, but can be released from this restraint once at the implantation site so that they can self-expand to their functional size. For example, a user can push the self-expanding valve out of a delivery sheath by, for example, actuating a pushing mechanism of the delivery assembly.

A loader or loading assembly can be used to load the prosthetic heart valve (e.g., the mechanically expandable or self-expanding prosthetic heart valve) in a radially compressed state into a delivery sheath or capsule of the delivery apparatus that is configured to contain and protect the prosthetic heart valve during delivery. For example, in some instances, a loading assembly can couple to an end of the delivery apparatus and be configured to receive an at least partially radially compressed or crimped prosthetic heart valve and facilitate transfer of the prosthetic heart valve into the delivery sheath or capsule of the delivery apparatus (or a distal end portion of the delivery apparatus that is configured to contain the prosthetic heart valve in the radially compressed state during delivery to the implantation site). However, in some examples, the coupling interface between the loading assembly and the distal end portion of the delivery apparatus can cause degradation to the delivery apparatus and/or may not provide a secure connection.

Accordingly, a need exists for an improved and more secure coupling interface between a loading assembly and a distal end portion of a delivery apparatus for a prosthetic medical device, such as a prosthetic heart valve.

SUMMARY

Described herein are examples of assemblies and methods for securing a loading assembly to a distal end portion of a delivery apparatus and loading a prosthetic medical device into a delivery capsule of the delivery apparatus using the loading assembly. In some examples, a coupling can be configured to connect the delivery capsule to a distal end of a shaft of the delivery apparatus and the coupling can include one or more channels depressed into an outer surface of the coupling. The loading assembly can comprise a loading capsule configured to be coupled to the coupling, the loading capsule having a proximal end portion comprising a plurality of axially extending flexible members that are configured to flex in a radial direction and couple with the one or more channels of the coupling member. The loading assembly can further comprise a collar disposed around the loading capsule and configured to couple to the plurality of flexible members and hold the plurality of flexible members in engagement with the one or more channels of the coupling. In some examples, a device housing configured to surround and house an at least partially radially expanded prosthetic medical device can be removably coupled to an end of the loading capsule.

In one representative example, a medical system comprises: a delivery apparatus for implanting a prosthetic medical device in a patient's body, the delivery apparatus comprising: a flexible shaft; a coupling attached to a distal end of the flexible shaft; and a delivery capsule coupled to the coupling and extending distally from the coupling, away from the distal end of the flexible shaft. The medical system further comprises a loading assembly comprising: a loading capsule comprising a plurality of axially extending flexible members configured to couple to an outer surface of the coupling and flex radially outward; and a collar disposed around the loading capsule and configured to lock the plurality of flexible members in engagement with the coupling such that the plurality of flexible members cannot flex radially outward.

In another representative example, a medical assembly comprises: a coupling configured to connect a delivery capsule to a distal end of a shaft of a delivery apparatus, the coupling including one or more channels depressed into an outer surface of the coupling. The medical assembly further comprises a loading capsule configured to be coupled to the coupling, the loading capsule having a proximal end portion comprising a plurality of axially extending flexible members spaced apart from one another around a circumference of the proximal end portion that are configured to flex in a radial direction and couple with the one or more channels of the coupling member. The medical assembly further comprises a collar disposed around the loading capsule and configured to slide along the loading capsule and couple to the plurality of flexible members and hold the plurality of flexible members in engagement with the one or more channels of the coupling.

In another representative example, a loading assembly for loading a radially expandable and compressible prosthetic medical device into a delivery apparatus comprises: a loading capsule having a proximal end portion comprising a plurality of axially extending flexible members spaced apart from one another around a circumference of the proximal end portion that are configured to flex in a radial direction and couple with a distal end portion of the delivery apparatus, a radially outward facing surface of one or more flexible members of the plurality of flexible members includes a first mating element; and a collar disposed around the loading capsule and configured to slide along the loading capsule, the collar comprising a second mating element configured to mate with and couple to the first mating element to prevent the plurality of flexible members from flexing radially outward.

In another representative example, a method comprises: moving a proximal end portion of a loading capsule of a loading assembly, the loading capsule comprising a plurality of axially extending flexible members, into contact with a coupling of a delivery apparatus and flexing the plurality of flexible members radially outward as a radially extending inner protrusion of each flexible member of the plurality of flexible members slides along an outer surface of the coupling, the coupling connecting a delivery capsule of the delivery apparatus to a distal end portion of a shaft of the delivery apparatus; and moving the plurality of flexible members radially inward such that the inner protrusion of each flexible member is engaged with one or more channels depressed into the outer surface of the coupling, thereby coupling the loading capsule to the coupling with the loading capsule surrounding the delivery capsule.

In another representative example, a loading assembly for loading a radially expandable and compressible prosthetic medical device into a delivery apparatus comprises: a loading capsule comprising an annular distal end portion and a proximal end portion configured to be coupled to the delivery apparatus; a loader coupled to the distal end portion of the loading capsule and comprising a tapered portion extending proximally into an interior of the distal end portion of the loading capsule; and a device housing removably coupled to the loading capsule, the device housing extending distally from the distal end portion of the loading capsule, and the device housing comprising an inner cavity configured to receive the prosthetic medical device in an at least partially radially expanded state.

In another representative example, a medical assembly comprises: a delivery apparatus comprising a delivery capsule, a flexible shaft, and a rigid coupling that connects the delivery capsule to the flexible shaft. The medical assembly further comprises a loading assembly comprising a loading capsule coupled to the coupling and a device housing removably coupled to the loading capsule and extending distally from the loading capsule. The medical assembly further comprises a radially expandable and compressible prosthetic heart valve disposed within and surrounded by the device housing, the prosthetic heart valve in an at least partially radially expanded configuration; and a sterile package containing the delivery apparatus, the loading assembly, and the prosthetic heart valve.

The foregoing and other objects, features, and advantages of the disclosed technology will become more apparent from the following detailed description, which proceeds with reference to the accompanying figures.

BRIEF DESCRIPTION OF THE DRAWINGS

FIG. 9A is a first perspective view of an example of a coupling configured to couple a delivery capsule and a distal end portion of a flexible shaft of a delivery apparatus to one another.

FIG. 9B is another perspective view of the coupling of FIG. 9A.

FIG. 10 is a side view of the coupling of FIG. 9A.

FIG. 11 is a side, cross-sectional view of the coupling of FIG. 9A.

FIG. 29 is a flow chart of a method for securing a loading assembly to a distal end portion of a delivery apparatus and loading a prosthetic medical device into a delivery capsule of the delivery apparatus using the loading assembly.

DETAILED DESCRIPTION

General Considerations

Figure 1:
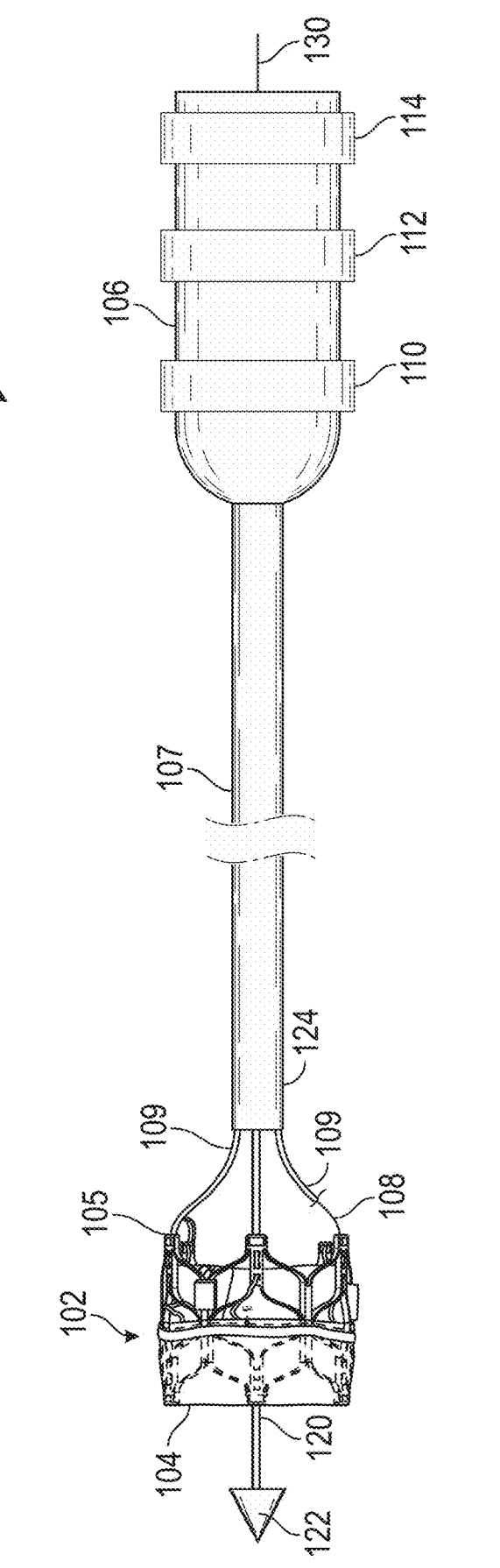
FIG. 1 is a side elevation view of a delivery apparatus for a prosthetic heart valve, according to one example.

For purposes of this description, certain aspects, advantages, and novel features of the examples of this disclosure are described herein. The described methods, systems, and apparatus should not be construed as limiting in any way. Instead, the present disclosure is directed toward all novel and non-obvious features and aspects of the various disclosed examples, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing examples. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over.

Nevertheless, it is still the same part and the object remains the same. As used herein, "and/or" means "and" or "or," as well as "and" and or.

As used herein, with reference to the prosthetic heart valve and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

Examples of the Disclosed Technology

Described herein are examples of a loading assembly that can be used to load a prosthetic medical device (such as a prosthetic heart valve), in a radially compressed configuration, into a delivery capsule or sheath at a distal end of a delivery apparatus. Also described herein are examples of an assembly for forming a secure (but removable) connection between the loading assembly and a distal end portion of a shaft of the delivery apparatus, thereby enabling a prosthetic heart valve or other prosthetic medical device to be easily loaded into the delivery capsule or sheath.

The disclosed loading assembly can include a loading capsule configured to be coupled to a coupling of the delivery apparatus, the coupling connecting the delivery capsule to the distal end portion of the shaft of the delivery apparatus. In some examples, the shaft of the delivery apparatus can be a flexible shaft that is steerable, and the coupling can be a rigid coupling (e.g., comprising a more rigid material than the flexible shaft). The loading assembly can further include a collar that is disposed around the loading capsule and configured to lock the loading capsule in engagement with the coupling, thereby creating a secure connection between the loading assembly and delivery apparatus and allowing a prosthetic medical device to be more easily loaded into the delivery capsule.

Also disclosed herein are examples of a device housing that can be removably coupled to a remainder of the loading assembly (e.g., the loading capsule) and configured to surround and house an at least partially radially expanded prosthetic medical device prior to radially compressing and loading the prosthetic medical device into the delivery capsule (e.g., during storage and/or transport or shipping of the assembly, prior to an implantation procedure).

Figure 2:
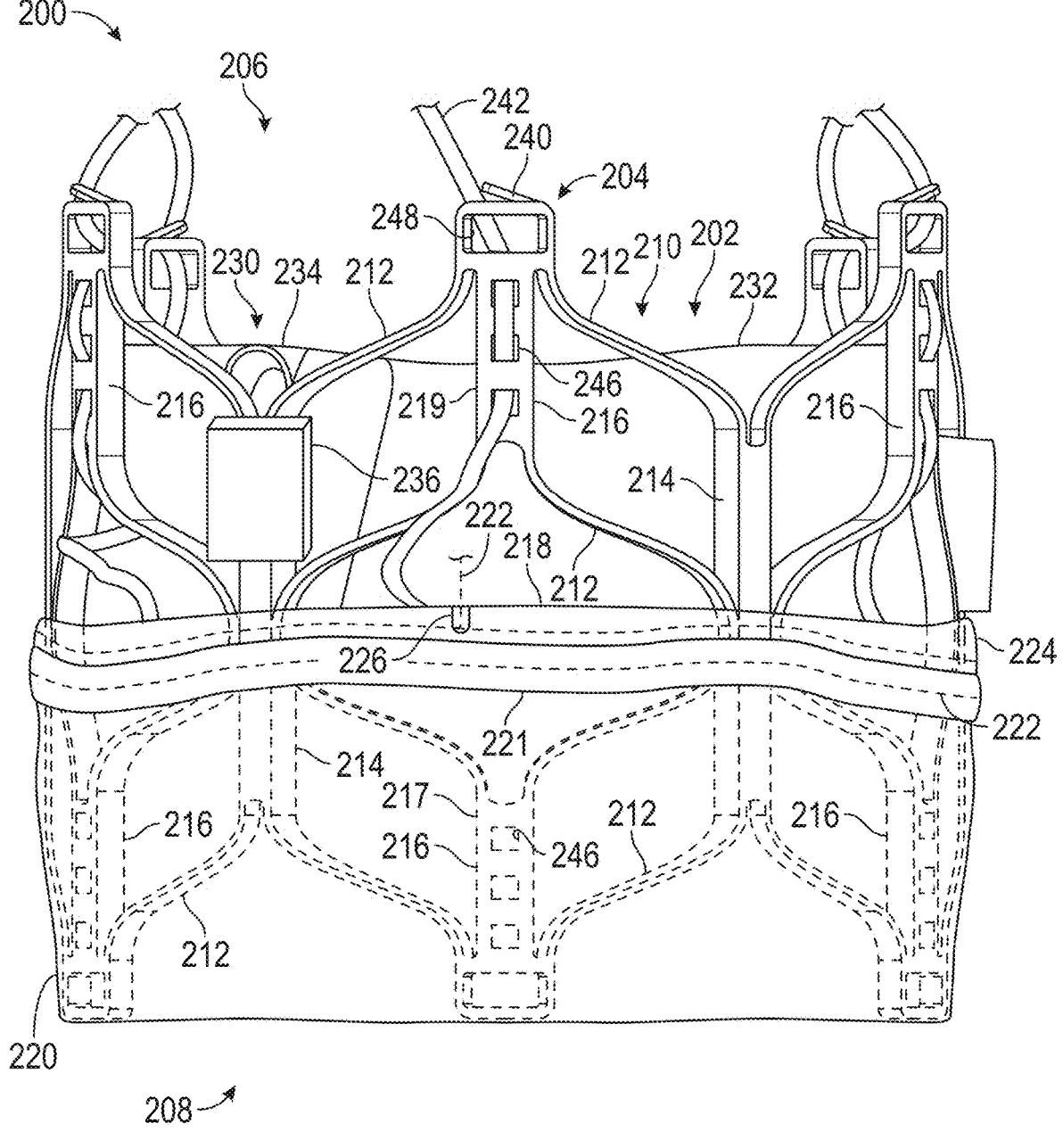
FIG. 2 is side perspective view of a prosthetic heart valve and an expansion assembly for the prosthetic heart valve, according to one example, where the prosthetic valve is locked in a radially expanded state.

In some examples, the delivery apparatus is configured to deliver and implant the prosthetic heart valve, such as the example prosthetic heart valve of FIG. 2, at a selected implantation site within a patient (e.g., within the native aortic valve, mitral valve, tricuspid valve or pulmonary valve). For example, by retracting the delivery capsule or sheath of the delivery apparatus (or a distal end portion of an outer shaft of the delivery apparatus) away from the radially compressed prosthetic heart valve, the prosthetic heart valve can expand to is expanded configuration and implant itself at the target implantation site.

FIG. 1 illustrates a delivery apparatus 100, according to one example, adapted to advance a prosthetic heart valve 102, such as prosthetic heart valve 200 described below with reference to FIG. 2, through a patient's vasculature and/or to deliver the prosthetic heart valve 102 to an implantation site (e.g., native heart valve) within a patient's body. The prosthetic heart valve 102 can be mounted on, retained within, and/or releasably coupled to a distal end portion of the delivery apparatus 100.

The prosthetic heart valve 102 can include a distal end 104 (which can be the inflow end of the prosthetic valve 102, such as when the prosthetic heart valve 102 is configured to replace a defective aortic valve when delivered transfemorally) and a proximal end 105 (which can be the outflow end of the prosthetic valve 102, such as when the prosthetic heart valve 102 is configured to replace a defective aortic valve when delivered transfemorally), wherein the proximal end 105 is positioned closer to a handle 106 of the delivery apparatus 100 than the distal end 104, and wherein the distal end 104 is positioned farther from the handle 106 than the proximal end 105. It should be understood that the delivery apparatus 100 and other delivery apparatuses disclosed herein can be used to implant prosthetic devices other than prosthetic valves, such as stents or grafts.

The delivery apparatus 100 in the illustrated example generally includes the handle 106, a first elongated shaft 107 (which comprises an outer shaft in the illustrated example) extending distally from the handle 106, one or more actuator members 108 extending distally through the shaft 107, and one or more support members 109 that can extend distally through the shaft 107 and can abut the proximal end 105 of the prosthetic valve 102. The delivery apparatus 100 can further include an inner shaft 120 extending from the handle 106 through the outer shaft 107 and a nose cone 122 connected to the distal end portion of the inner shaft 120.

In some examples, the inner shaft 120 can define a guidewire lumen that is configured to receive a guidewire 130. The delivery apparatus can be advanced over the guidewire 130 toward a target implantation site in a patient.

Each actuator member 108 can have a distal end connected to the distal end 104 of the prosthetic valve 102. Each of the actuator members 108 can extend through a respective support member 109 and together can define a respective actuator assembly that can extend through the shaft to the handle 106. In alternative examples, the actuator members 108 and the support members 109 need not be co-axial with respect to each and instead can extend side-by-side through the shaft.

The actuator members 108 and/or the support members 109 can be configured to radially expand the prosthetic heart valve 102 by bringing the ends 104, 105 of the prosthetic valve 102 closer together (i.e., squeezing the prosthetic valve 102 axially) thereby axially foreshortening and radially expanding the prosthetic valve 102. As one example, the actuator members 108 can be configured to be actuated to provide a proximally directed (e.g., pulling) force to the distal end 104 of the prosthetic valve 102 while the one or more support members 109 can be configured to provide a countervailing distally directed (e.g., pushing) force to the proximal end 105 of the prosthetic valve 102. As one such example, a physician can pull the actuator members 108 to provide the proximally directed force to the distal end 104 of the prosthetic valve 102, while simultaneously gripping, holding, and/or pushing the handle 106 to provide the countervailing distally directed force to the proximal end 105 of the prosthetic valve 102.

As described in greater detail below, the actuator members 108 can cooperate with a locking element on the prosthetic valve 102 to retain the prosthetic valve in a radially expanded state.

The actuator members 108 can comprise a suture, string, cord, wire, cable, or other similar device that can transmit a pulling force from the handle 106 to the prosthetic valve when actuated by a physician. The support members 109 can comprise a relatively more rigid component, such a tube that can abut the proximal end 105 of the prosthetic valve 102 and resist proximal movement of the prosthetic valve relative to the shaft 107 when a proximal pulling force is applied to the actuator members 108.

Although two actuator members 108 and two support members 109 are shown in FIG. 1, it should be understood that the delivery apparatus 100 can include more or less than two actuator members 108 and/or two support members 109, in other examples. As just one example, the delivery apparatus 100 can include six actuator members 108 and/or six support members 109. In other examples, a greater or fewer number of actuator members 108 and/or support members 109 can be present, such as three, four, five, seven, and/or eight actuator members 108 and/or three, four, five, seven, and/or eight support members 109. In some examples, the delivery apparatus 100 can include equal numbers of actuator members 108 and support members 109. However, in other examples, the delivery apparatus 100 can include a different number of actuator members 108 than support members 109.

The prosthetic valve 102 can be at least partially self-expanding, in some examples. That is, the prosthetic valve 102 can be configured to self-expand from a radially compressed, delivery state to at least a partially radially expanded state. In one example, the prosthetic valve 102 can be configured to self-expand to a partially radially expanded state, and the actuator members 108 can be actuated to further radially expand the prosthetic valve to the fully radially expanded state. Thus, in such examples, the prosthetic valve 102 can be both mechanically expandable and self-expanding. As another such example, the prosthetic valve 102 can be configured to self-expand to the fully radially expanded state and the actuator members 108 can be actuated to only lock the prosthetic valve 102 in the fully radially expanded state. When configured to be self-expanding, the frame of the prosthetic valve 102 can be constructed from a shape-memory material (e.g., Nitinol) that biases the prosthetic valve 102 towards a radially expanded state. That is, the prosthetic valve 102 can be shape set in a partially radially expanded state or the fully radially expanded state (e.g., not the radially compressed state) so that the prosthetic valve 102 returns to the shape set radially expanded state when released from a restraining mechanism (e.g., lasso, sheath, etc.).

However, in other examples, the prosthetic valve 102 may not be self-expanding. For example, the frame of the prosthetic valve can be made from a plastically expandable material and can retain the prosthetic valve in its radially compressed state until expanded by the actuator members 108. In such examples, the actuator members 108 can be configured to expand the prosthetic valve all of the way from the crimped state to the fully radially expanded state.

In other examples, the frame of the prosthetic valve 102 can comprise a plurality of overlapping struts that are pivotably connected to each other at hinges where the struts overlap with each other, as further described in U.S. Publication Nos. 2018/0153689 and 2020/0188099, which are incorporated herein by reference. In some examples, the struts can be configured and connected to each other such that the prosthetic valve remains in a radially compressed state until expanded by actuation of the actuator members 108. In other examples, the struts can be configured and connected to each other such that the frame has some inherent resiliency that causes the frame to self-expand to at least a partially radially expanded state when released from a constraining member (e.g., a delivery sheath or capsule).

In some examples, the shaft 107 can be configured as a steerable guide catheter having an adjustable curvature for use in steering the delivery apparatus 100 through the patient's vasculature. In particular examples, the shaft 107 can include a steerable distal section (also referred to herein as a flexible section comprising a compliant and flexible material), the curvature of which can be adjusted by the operator to assist in guiding the apparatus through the patient's vasculature. The delivery apparatus 100 can, for example, include a steering member (e.g., a steering wire or cable) that extends along or through a lumen of the shaft and has a proximal end portion operatively coupled to a steering mechanism on the handle and a distal end portion fixed to the steerable distal section of the shaft 107. The steering mechanism is configured to adjust the tension of the steering member, which in turn is effective to adjust the curvature of the steerable distal section of the shaft. Further details regarding steering mechanisms and steerable shafts for a delivery apparatus are disclosed in U.S. Publication No. 2013/0030519 and U.S. Pat. No. 10,076,638, which are incorporated herein by reference.

In some examples, the shaft 107 can have a distal end portion 124 sized to house the prosthetic valve in its radially compressed, delivery state during delivery of the prosthetic valve through the patient's vasculature. In this manner, the distal end portion 124 functions as a delivery sheath or capsule for the prosthetic valve during delivery, and as such may be referred to herein as the delivery sheath (or capsule) 124.

The handle 106 of the delivery apparatus 100 can include one or more control mechanisms (e.g., knobs or other actuating mechanisms) for controlling different components of the delivery apparatus 100 in order to implant the prosthetic heart valve 102. For example, in the illustrated example the handle 106 can comprise one or more of first, second, and third knobs 110, 112, and 114.

When included, the first knob 110 can be configured to produce axial movement of the shaft 107 relative to the prosthetic heart valve 102 in the distal and/or proximal directions in order to deploy the prosthetic valve 102 from the delivery sheath 124 once the prosthetic valve 102 has been advanced to a location at or adjacent the desired implantation location within the patient's body. For example, actuating the first knob 110 in a first direction (e.g., clockwise) can retract the shaft 107 proximally relative to the prosthetic heart valve 102 and actuation of the first knob 110 in a second direction (e.g., counter-clockwise) can advance the shaft 107 distally. The first knob 110 can be actuated by rotating the knob 110 as indicated above, or by sliding or moving the first knob 110 axially, such as by pulling and/or pushing the knob.

When included, the second knob 112 can be configured to actuate the actuator members 108 to radially expand and/or lock the prosthetic heart valve 102. For example, actuating the second knob 112 can pull the actuator members 108 proximally relative to the support members 109, thereby radially expanding the prosthetic heart valve 102 and locking the prosthetic heart valve 102 in its current state/position. The second knob 112 can be actuated by rotating the second knob 112, or by sliding or moving the second knob 112 axially, such as by pulling and/or pushing the knob.

In other examples, the second knob 112 may not be included, and a physician can expand and/or lock the prosthetic heart valve 102 by directly actuating (e.g., pulling) the actuator members 108. In such examples, the actuator members 108 can extend through and/or out of the handle 106 so that they are directly accessible to the physician and/or can be easily pulled by the physician. After radially expanding and locking the heart valve 102, the physician can cut the actuator members 108, such as at and/or near a locking element (e.g., locking element 240 described below) of the heart valve 102. The delivery apparatus 100 can include one or more cutting elements that can be actuated by the user to cut the actuator members 108 near the prosthetic valve, such as disclosed in U.S. Publication No. 2018/0153689.

When included, the third knob 114 can be configured to be actuated to retain the prosthetic heart valve 102 in its expanded configuration. For example, the third knob 114 can be operatively connected to a locking tool and can be actuated (e.g., rotated) to move the locking tool from a disengaged to an engaged state (to lock the prosthetic valve 102) and/or from the engaged state to the disengaged state (to unlock the prosthetic valve 102). For example, a physician can lock the prosthetic valve 102 to prevent the prosthetic valve 102 from collapsing and/or can unlock the prosthetic valve 102 to compress and/or reposition the prosthetic valve 102 relative to the native tissue. The third knob 114 can be actuated by rotating the third knob 114, or by sliding or moving the third knob 114 axially, such as by pulling and/or pushing the knob.

However, in other examples, the third knob 114 may not be included. In some such examples, the prosthetic valve 102 can be self-locking and may not require any action from the physician to lock at a particular valve diameter. That is, the locking mechanism can automatically and/or continuously lock the prosthetic valve 102 at a range of valve diameters, without needing to be engaged/activated by the physician. For example, one such self-locking locking mechanism is shown in FIG. 2.

FIG. 2 illustrates an example of a transcatheter prosthetic heart valve 200 that can be delivered to an implantation site (e.g., native heart valve) through a patient's vasculature (e.g., veins or arteries) using a delivery apparatus, such as the delivery apparatus 100 described above with reference to FIG. 1. The prosthetic heart valve 200 includes a radially expandable and compressible annular frame 202 and an expansion and locking assembly 204 that is configured to radially expand the prosthetic heart valve 200 and to lock the frame 202 at one or more valve diameters to prevent radial compression/collapse of the prosthetic heart valve 200.

The prosthetic heart valve 200 includes an outflow end 206 opposite an inflow end 208. When implanted in a native heart valve or vessel, blood is configured to flow from the inflow end 208 to the outflow end 206. In some examples, such as where the prosthetic heart valve 200 is delivered to a native aortic valve through the aorta, the outflow end 206 can be a proximal end 206 of the prosthetic heart valve 200 (the end closer to the delivery apparatus) and the inflow end 208 can be a distal end 208 of the prosthetic heart valve 200 (the end furthest from the delivery apparatus). In other examples, such as where the heart valve is delivered to a native mitral valve through the atrial septum and right atrium or to the native aortic valve through the apex of the heart, the outflow end 206 can be a distal end 206 of the prosthetic heart valve 200 and the inflow end 208 can be a proximal end 208 of the prosthetic heart valve 200.

The prosthetic heart valve 200 is radially compressible and expandable between a radially compressed state and a radially expanded state (FIG. 2). The prosthetic heart valve 200 can be advanced through a patient's vasculature in the radially compressed state and can then be radially expanded at the implantation site (e.g., aortic and/or mitral valve) to the radially expanded state. The radially expanded state can be a fully radially expanded state where the prosthetic heart valve 200 is configured to circumferentially contact and/or create a seal with the surrounding native tissue (when implanted at the implantation site) such that blood only flows through the prosthetic heart valve 200 and does not flow around the prosthetic heart valve 200, between the prosthetic heart valve 200 and the native tissue.

The prosthetic heart valve 200 also can be configured to be radially expanded to, and locked in, one or more partially radially expanded states, between the radially compressed state and the radially expanded state. As just one example, such as where the prosthetic heart valve 200 is configured to be partially self-expanding, the prosthetic heart valve 200 can be configured to self-expand to a first partially radially expanded state and can then be mechanically expanded to, and continuously locked in, a plurality of partially radially expanded states between the first partially radially expanded state and the radially expanded state. As another example, such as where the prosthetic heart valve 200 is not self-expanding, the prosthetic heart valve 200 can be configured to be mechanically expanded and continuously locked in a plurality of a partially radially expanded states between the radially compressed state and the radially expanded state.

The frame 202 of the prosthetic heart valve 200 can include a plurality of struts 210 defining a plurality of windows or openings. The struts 210 can include rows of angled struts 212 that extend between a first set of vertical struts or posts 214 and a second set of vertical struts or posts 216. The first and second sets of vertical struts 214, 216 can extend axially between the outflow end 206 and the inflow end 208 of the prosthetic heart valve 200. The first set of vertical struts or posts 214 can be configured to at least partially form, support, and/or define one or more commissures of the leaflet assembly of the prosthetic heart valve 200. The second set of vertical struts or posts 216 can be configured to at least partially form, support, and/or define the expansion and locking assembly 204. In this way, the expansion and locking assembly 204 can be at least partially integrated/incorporated into the frame 202 of the prosthetic heart valve 200, thereby reducing the diameter and/or profile of the frame 202 in the radially compressed (i.e., crimped) state.

The second set of vertical struts 216 can comprise two separate rows of struts that are axially spaced from one another, namely a first row of vertical struts 217 at the inflow end 208 of the frame 202, and a second row of vertical struts 219 at the outflow end 206 of the frame 202. As will be explained in greater detail below, the expansion and locking assembly 204 can extend axially between these two rows of vertical struts 217, 219 to pull the inflow and outflow ends 208, 206 of the frame 202 towards one another to radially expand the prosthetic heart valve 200. Because the first row of vertical struts 217 form and/or define the inflow end portion of the frame, the first row of vertical struts 217 also can be referred to herein as the inflow end portion 217 of the frame 202. Similarly, the second row of vertical struts 219 also can be referred to herein as the outflow end portion 219 of the frame 202.

The frame 202 can be made of any of various suitable plastically-expandable materials (e.g., stainless steel, etc.) or self-expanding materials (e.g., nickel titanium alloy (NiTi), such as nitinol) as known in the art. When constructed of a plastically-expandable material, the frame 202 (and thus the prosthetic heart valve 200) can be crimped to the radially compressed state on a delivery apparatus and then expanded inside a patient by, for example, the expansion and locking assembly 204. When constructed of a self-expandable material, the frame 202 (and thus the prosthetic heart valve 200) can be crimped to the radially compressed state and restrained in the radially compressed state by a lasso, delivery sheath or capsule, and/or other restraining mechanism. Once inside the body, the restraining force of the restraining mechanism can be released (e.g., reducing tension in a lasso or deploying the prosthetic valve from a sheath), which allows the prosthetic heart valve 200 to radially expand.

Suitable plastically-expandable materials that can be used to form the frame 202 include, without limitation, stainless steel, a biocompatible, high-strength alloy (e.g., a cobalt-chromium or a nickel-cobalt-chromium alloys), polymers, or combinations thereof. In particular examples, frame 202 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight.

The prosthetic heart valve 200 can include a skirt assembly 218 that is configured to cover the openings of the frame 202 and provide a seal between the frame 202 and the surrounding native tissue. The skirt assembly 218 can extend from and/or around the inflow end 208 of the prosthetic heart valve 200 along the inner and/or outer sides of the frame 202 (towards the outflow end 206 of the prosthetic heart valve 200). The skirt assembly 218 can include an outer skirt 220 that extends circumferentially around the outer surface of the frame.

The outer skirt 220 can extend from the inflow end 208 of the prosthetic heart valve 200 along the outer surface of the frame and can be secured to the frame 202, such as via sutures. For example, the outer skirt 220 can be sutured to the angled struts 212, the vertical struts 214, and/or to an inner skirt (not shown) that is positioned on the opposite surface of the frame. In some examples, the outer skirt 220 can extend from the inflow end 208 towards the outflow end 206 but can stop short of the flexible connectors (e.g., flexible connectors 236 described below) that hold the commissures of the leaflets of the prosthetic valve to the frame.

In some examples, the skirt assembly 218 can include an inner skirt (not shown) that can extend from the inflow end 208 of the prosthetic heart valve 200 along the inner surface of the frame 202 and can be secured to the frame 202, such as via sutures. For example, the inner skirt can be sutured to the angled struts 212, the vertical struts 214, and/or can be sutured to the outer skirt 220.

The skirt assembly 218 can be formed of and/or constructed from one or more materials that are flexible enough to allow for radial compression and expansion of the frame 202 and/or that are tough enough to resist tearing and prevent paravalvular leakage (PVL). As examples, the skirt assembly 218 can be formed of and/or constructed from one or more of foam, cloth, fabric, pericardial tissue, and/or polymers, such as such as polyethylene terephthalate (PET) and/or an expanded polytetrafluoroethylene (ePTFE). In some examples, the skirt assembly 218 can be configured to promote tissue ingrowth to further enhance the seal between the prosthetic heart valve 200 and the native heart valve tissue. For example, the portion of the skirt assembly 218 included on the outer side of the frame 202 (e.g., the outer skirt) can includes pores and/or can be impregnated with growth factors such as transforming growth factor alpha (TGF-alpha) to promote tissue ingrowth.

The outer skirt 220 can include a sleeve 221 that is configured to receive a restraining mechanism (e.g., a tension member such as in the form of a lasso or adjustable loop) 222, such as in examples where the prosthetic heart valve 200 is self-expanding and requires a restraining mechanism 222 to hold the prosthetic heart valve 200 in the radially compressed state and/or to control expansion of the prosthetic valve. As one example, the sleeve 221 can form a pocket in the outer skirt 220 that extends circumferentially around the frame 202. The sleeve 221 can be included at an outflow edge portion 224 of the outer skirt. The sleeve 221 can be formed by folding the outflow edge portion back against the main body of the skirt and then connecting (e.g., stitching) the folded flap against the main body of the skirt. The sleeve 221 desirably is positioned approximately halfway between the inflow end 208 and the outflow end 206 of the prosthetic heart valve 200 so that the restraining force of the retraining mechanism is equally distributed along the length of the frame.

The restraining mechanism 222 can extend through the sleeve 221 and circumferentially around the frame 202. The restraining mechanism 222 can exit the sleeve 221 via an opening 226 in the skirt assembly 218. From the opening 226, the restraining mechanism 222 can extend proximally towards the handle of the delivery apparatus and can be configured to be adjusted by the physician to allow the prosthetic heart valve 200 to be radially expanded. For example, the physician can loosen the restraining mechanism 222 to allow the prosthetic heart valve 200 to radially self-expand and/or to be mechanically radially expanded. The restraining mechanism 222 can be adjusted between a constrained state in which the restraining mechanism 222 is configured to hold the prosthetic heart valve 200 in the radially compressed state and a loosened state in which the restraining mechanism 222 is configured to allow the prosthetic heart valve 200 to radially expand.

The prosthetic heart valve 200 can include a leaflet assembly 230 comprising leaflets 232. The leaflets 232 are configured to selectively open and close to regulate the flow of blood through the prosthetic heart valve 200. In the illustrated example, the leaflet assembly 230 can include three flexible leaflets 232, although a greater or a smaller number of leaflets can be used. The leaflets 232 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein. Additional information regarding the leaflets 232, as well as additional information regarding the material of the skirt assembly 218, can be found, for example, in U.S. Pat. No. 10,195,025, which is incorporated herein by reference.

The leaflets 232 can be secured to one another at their adjacent sides to form commissures 234. The prosthetic heart valve 200 can include flexible connectors 236 that can be used to mount the leaflets 232 to the vertical struts 214 at the commissures 234 and/or to interconnect pairs of adjacent sides of the leaflets 232. For example, the prosthetic heart valve 200 can include three flexible connectors 236 to secure each of the three leaflets 232 to the frame 202 at the three commissures 234. The flexible connectors 236 can be mounted to the vertical struts 214 more proximate the outflow end 206 than the inflow end 208, between adjacent rows of the angled struts 212. The inflow edge portions of the leaflets 232 can be secured to the frame 202, such by stitching the inflow edge portions leaflets directly to selected struts of the frame, or by stitching the inflow edge portions of the leaflets to an inner skirt, which in turn is connected to selected struts of the frame with sutures. Further details regarding the formation of the commissures and connecting the commissures and the inflow edge portions of the leaflets are disclosed in U.S. Patent Application Nos. 63/085,947, 63/139,514, and 63/026,866, and in to-be-filed U.S. patent application entitled "PROSTHETIC HEART VALVE", which are incorporated herein by reference.

As introduced above, the expansion and locking assembly 204 is configured to radially expand the prosthetic heart valve 200, such as after the restraining mechanism 222 has been loosened, and to lock/hold the prosthetic heart valve 200 in a radially expanded state. For example, in operation, a physician can first loosen the restraining mechanism 222 (in examples where the prosthetic heart valve 200 is self-expanding), and can then adjust the expansion and locking assembly 204 to further radially expand the prosthetic heart valve 200 and to lock the prosthetic heart valve 200 in a radially expanded state.

The expansion and locking assembly 204 can comprise a locking element 240 and an actuator member 242. The actuator member 242 is coupled to the frame at first location (which can be at or closer to the inflow end of the frame) and at a second location by the locking element 240 (which can be at or closer to the outflow end of the frame), wherein the second location is axially spaced from the first location. In particular, the actuator member 242 is fixedly secured to the frame 202 at the first location and slidably coupled to the locking element 240 at the second location such that actuator member 242 can be pulled in a proximal direction relative to the locking element 240. The locking element 240 is configured to hold/lock the prosthetic heart valve 200 in a radially expanded state to prevent radial compression of the frame 202 by preventing movement of the actuator member 242 in the distal direction relative to the locking element 240. The actuator member 242 is configured to be selectively adjusted (e.g., pulled) to move the proximal direction to cause radial expansion of the frame 202 or to simply the lock the frame in the radially expanded state if the frame 202 is fully self-expandable. For example, a physician can pull the actuator member 242 proximally to radially expand the prosthetic heart valve 200.

The actuator member 242 desirably comprises a flexible tension member, such as a suture (such as a Dyneema® suture), string, cord, wire, cable, or other similar device that can be readily pulled by a physician to radially expand the prosthetic heart valve 200 and can be the same as, or similar to, actuator members 108 described above with reference to FIG. 1. Thus, the proximal end portions of the actuator members 242 can extend to a handle (e.g., handle 106) of a delivery apparatus and can be operatively connected to a knob (e.g., knob 112) or other control member on the handle to control the amount of tension applied to the actuator members 242. In some examples, the prosthetic heart valve 200 can include six actuator members 242. However, in other examples, the prosthetic heart valve 200 can include more or less than six actuator members 242.

The actuator members 242 can be coupled to the frame 202, and more specifically, can be coupled the frame 202 at or near the inflow and outflow ends 208, 206 of the frame, such that pulling of the actuator members 242 in the proximal direction while applying a distally directed force to the frame (e.g., via support members 109) causes the frame 202 to axially foreshorten and radially expand. As one example, the actuator members 242 can extend through openings 246 and/or 248 in the frame 202 at or near the inflow and outflow ends 208, 206 of the prosthetic heart valve 200. The openings 246, 248 can extend radially all of the way through the frame (from the inner side of the frame 202 to the outer side of the frame 202). In some examples, the openings 246 and/or 248 can be formed in the frame 202 by, for example, laser cutting. However, in other examples, the openings 246 and/or 248 can be formed by other removal means, such as die cutting, machining, etc., and/or can be integrally formed in the frame 202 during formation of the frame, such as via a molding process.

The openings 246, 248 can be included in the vertical struts 216 of the frame 202 and can be axially spaced from one another. However, in other examples, the actuator member 242 need not extend through the openings in the frame 202 and instead can extend next to the frame 202 and can be coupled to the vertical struts 216 via fasteners, adhesives, welding, and/or other fastening means. Each of the actuator members 242 can be coupled to, and extend between, one of the vertical struts in the first row of vertical struts 217 and one of the vertical struts in the second row of vertical struts 219 that are circumferentially aligned with one another. The actuator member 242 can extend axially between the vertical struts 217 on the inside of the outer skirt, such between the outer skirt and the outer surface of the frame, or along the inner surface of the frame, and/or on the outside of the outer skirt.

In operation, the prosthetic heart valve 200 can be loaded/mounted onto a distal end portion of the delivery apparatus (e.g., delivery apparatus 100 of FIG. 1) in the radially compressed (crimped) state. In some examples, the restraining mechanism 222 (e.g., lasso) can be used to hold the prosthetic heart valve 200 in the radially compressed state. The prosthetic heart valve 200 can be loaded inside a delivery sheath or capsule (e.g., delivery sheath 124 of FIG. 1) of the delivery apparatus (as described in greater detail below with reference to FIGS. 3A-B, 12A-12C, and 29-31). The prosthetic heart valve 200 can then be advanced through the patient's vasculature by the delivery apparatus until it reaches the implantation site (e.g., native aortic valve). As one example, the prosthetic heart valve 200 can be delivered to the native aortic valve, such as transfemorally. For example, the prosthetic heart valve 200 can be introduced into a femoral artery through an incision in a patient's groin and can then be advanced through the femoral artery to the aortic valve via the iliac artery and aorta. As another example, the prosthetic heart valve 200 can be introduced to the native mitral valve, such as transfemorally. For example, the prosthetic heart valve 200 can be introduced into a femoral vein through an incision in a patient's groin and can then be advanced through the femoral vein to the mitral valve via the inferior vena cava, the right atrium, and an opening in the atrial septum. In other examples, the prosthetic heart valve 200 can be implanted in various other locations, such as in the native tricuspid valve, within the superior vena cava or inferior vena cava (for replacing the function of the native tricuspid valve), within the native pulmonary valve, or within the pulmonary artery (for replacing the function of the native pulmonary valve).

Use of a delivery sheath (or capsule) to restrain the prosthetic valve (in addition to the restraining mechanism) during delivery can be advantageous in that the delivery sheath can provide an atraumatic covering for the prosthetic valve as it is advanced through the patient's vasculature. Once deployed from the delivery sheath at or near the implantation site, the restraining mechanism continues to hold the prosthetic valve in the radially compressed state during final positioning of the prosthetic valve. In other examples, the restraining mechanism can be removed, and the prosthetic valve can be retained in a radially compressed state only with the delivery sheath.

Upon reaching the implantation site, the physician can begin the deployment process, which can include deploying the prosthetic valve from the delivery sheath (if contained within a sheath or capsule) and then releasing the prosthetic heart valve from the restraining mechanism 222, radially expanding the prosthetic heart valve 200 to the fully radially expanded state and locking the prosthetic heart valve 200 in the fully radially expanded state. In examples where the restraining mechanism 222 is included, such as in examples where the prosthetic heart valve 200 is at least partially self-expanding, the physician can start the deployment process by loosening the restraining mechanism 222, allowing the prosthetic valve to radially expand to a partially expanded state. In the partially expanded state there may be some slack in the actuator members 242. Specifically, as the prosthetic heart valve 200 self-expands, the inflow and outflow ends 208, 206 of the frame 202 may be drawn towards one another, thereby creating slack in the actuator members 242 due to the fact that the actuators 242 are secured to the struts 217 at the inflow end portion of the prosthetic heart valve 200 and are held by the locking elements 240 at the outflow end portion of the prosthetic heart valve 200. In other words, during the initial expansion of the prosthetic valve, the actuators 242 are not pulled or moved proximally through the locking elements 240 to take up slack in the actuator members as the prosthetic valve expands. Thus, in the radially compressed state the actuator members 242 may be in a taught state, and as the prosthetic heart valve 200 radially self-expands and axially foreshortens, the actuator members 242 may relax to a loosened state in which slack exists in the actuator members 242.

If needed, the prosthetic heart valve can be recompressed to a smaller diameter or to the fully compressed state by actuating the restraining mechanism 222 for re-positioning the prosthetic valve or for withdrawing the prosthetic out of the patient (in which case, the prosthetic valve can be first withdrawn back into the delivery sheath and then withdrawn from the patient's body). Advantageously, due to the slack in the actuator members 242 in the partially expanded state, the prosthetic valve can be recompressed to a smaller diameter or to the fully compressed state without having to manipulate or unlock the actuator members 242 from the locking elements 240.

After the prosthetic heart valve has been positioned at the desired implantation location and expanded to the partially expanded state, the physician may begin to mechanically radially expand the prosthetic valve by, for example, pulling the actuator members 242 proximally and/or by providing a countervailing distally directed pushing force to the outflow end 206 of the prosthetic heart valve 200 via, for example, the support members 109 (FIG. 1). As the physician pulls the actuator members 242 proximally relative to the frame 202 and the support members, the inflow and outflow ends 208, 206 of the frame 202 may be drawn towards one another as the prosthetic heart valve 200 radially expands. The proximally directed force provided by the physician initially removes the slack from the actuator members 242 and draws the actuator members 242 taught, which locks the prosthetic heart valve 200 (i.e., prevent radial re-compression of the prosthetic heart valve 200). Then, once the actuator members 242 are drawn taught, the physician can continue pulling the actuator members 242 proximally to mechanically radially expand the prosthetic heart valve 200.

Once the actuator members 242 are drawn taught and are engaged with the locking elements 240, the prosthetic heart valve 200 cannot be radially re-compressed, unless the physician selectively disengages the actuator members 242 from the locking elements 240 and tightens the restraining mechanism 222.

After locking the prosthetic heart valve 200 in the radially expanded state, a physician can cut and/or otherwise sever the actuator members 242, such as at and/or near the locking element 240 and withdraw and/or remove the delivery assembly (e.g., delivery apparatus 100 of FIG. 1), including the support members (e.g., support members 109 of FIG. 1), from the patient.

The preceding description describes a method for implanting a prosthetic valve using the disclosed delivery apparatuses to the native aortic valve via transfemoral delivery. However, it should be understood that the disclosed delivery apparatuses can be used to deliver a prosthetic valve (or another type of implantable medical device) to other native annulus of the heart (the pulmonary, mitral, and tricuspid valves), to vessels communicating with the heart (pulmonary artery, the inferior vena cava, or the superior vena cava), or to other locations within the body, using any of various delivery techniques.

For example, a prosthetic valve can be implanted within the native aortic valve in a transapical procedure, whereby the prosthetic valve (on the distal end portion of the delivery apparatus) is introduced into the left ventricle through a surgical opening in the chest and the apex of the heart and the prosthetic valve is positioned within the native aortic valve. Alternatively, in a transaortic procedure, a prosthetic valve (on the distal end portion of the delivery apparatus) are introduced into the aorta through a surgical incision in the ascending aorta, such as through a partial J-sternotomy or right parasternal mini-thoracotomy, and then advanced through the ascending aorta toward the native aortic valve.

For implanting a prosthetic valve within the native mitral valve via a transseptal delivery approach, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, into the right atrium, across the atrial septum (through a puncture made in the atrial septum), into the left atrium, and toward the native mitral valve. Alternatively, a prosthetic valve can be implanted within the native mitral valve in a transapical procedure, whereby the prosthetic valve (on the distal end portion of the delivery apparatus) is introduced into the left ventricle through a surgical opening in the chest and the apex of the heart and the prosthetic valve is positioned within the native mitral valve.

For implanting a prosthetic valve within the native tricuspid valve, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, and into the right atrium, and the prosthetic valve is positioned within the native tricuspid valve. A similar approach can be used for implanting the prosthetic valve within the native pulmonary valve or the pulmonary artery, except that the prosthetic valve is advanced through the native tricuspid valve into the right ventricle and toward the pulmonary valve/pulmonary artery.

Another delivery approach is a transatrial approach whereby a prosthetic valve (on the distal end portion of the delivery apparatus) is inserted through an incision in the chest and an incision made through an atrial wall (of the right or left atrium) for accessing any of the native heart valves. Atrial delivery can also be made intravascularly, such as from a pulmonary vein. Still another delivery approach is a transventricular approach whereby a prosthetic valve (on the distal end portion of the delivery apparatus) is inserted through an incision in the chest and an incision made through the wall of the right ventricle (typically at or near the base of the heart) for implanting the prosthetic valve within the native tricuspid valve, the native pulmonary valve, or the pulmonary artery.

In all delivery approaches, the delivery apparatus can be advanced over a guidewire (e.g., guidewire 130 shown in FIG. 1) previously inserted into a patient's vasculature and/or an introducer sheath previously inserted into the patient's vasculature. Moreover, the disclosed delivery approaches are not intended to be limited. Any of the prosthetic valves disclosed herein can be implanted using any of various delivery procedures and delivery devices known in the art.

In some examples, a prosthetic heart valve, such as the prosthetic heart valve 200 of FIG. 2, can be loaded into a delivery capsule or sheath coupled to or forming a distal end portion of a shaft of a delivery apparatus (e.g., delivery apparatus 100 of FIG. 1) in the radially compressed configuration using a loader or loading assembly. Such a loading assembly can couple to the distal end portion of a shaft of the delivery apparatus (e.g., shaft 107 of FIG. 1) and be configured to receive the prosthetic heart valve (which may be at least partially radially compressed, e.g., from crimping) and further compress and load the prosthetic heart valve into the delivery capsule or sheath of the delivery apparatus.

However, since the shaft of the delivery apparatus (which in some examples can be an outer shaft of the delivery apparatus) which the loading assembly couples to can be a steerable and flexible shaft (e.g., comprising a softer polymeric material that is configured to flex or bend during delivery to navigate turns and bends of a patient's anatomy) and the loading assembly can comprise a harder material than the flexible shaft (e.g., a hard plastic), coupling the loading assembly directly to the outer shaft can result in compression set on the material of the flexible shaft. As used herein, compression set can refer to a permanent or semi-permanent indentation of the flexible shaft of the delivery apparatus that reduces the frictional forces that hold the delivery apparatus in place relative to the loading apparatus, thereby resulting in a less secure coupling interface (and connection) between the loading assembly and the delivery apparatus.

FIGS. 3-15 show examples of a loading assembly and a coupling joining a distal end of a (flexible and/or steerable) shaft of the delivery apparatus and a delivery capsule of the delivery apparatus. Together, the loading assembly and coupling are configured to provide a more secure connection interface between the delivery apparatus and the loading assembly, while avoiding compression set and/or other degradation to the delivery apparatus while loading a prosthetic heart valve (or another prosthetic medical device, such as a stent) into the delivery capsule using the loading assembly. In some examples, the shaft of the delivery apparatus to which the coupling is coupled is a steerable shaft of the delivery apparatus, such as first shaft 107 shown in FIG. 1 and a distal end portion of the shaft which is coupled to the coupling can be flexible and configured to bend as it is steered through vasculature and/or a heart of a patient. In some examples, the shaft is an outer shaft of the delivery apparatus.

Figures 3A, 3B:
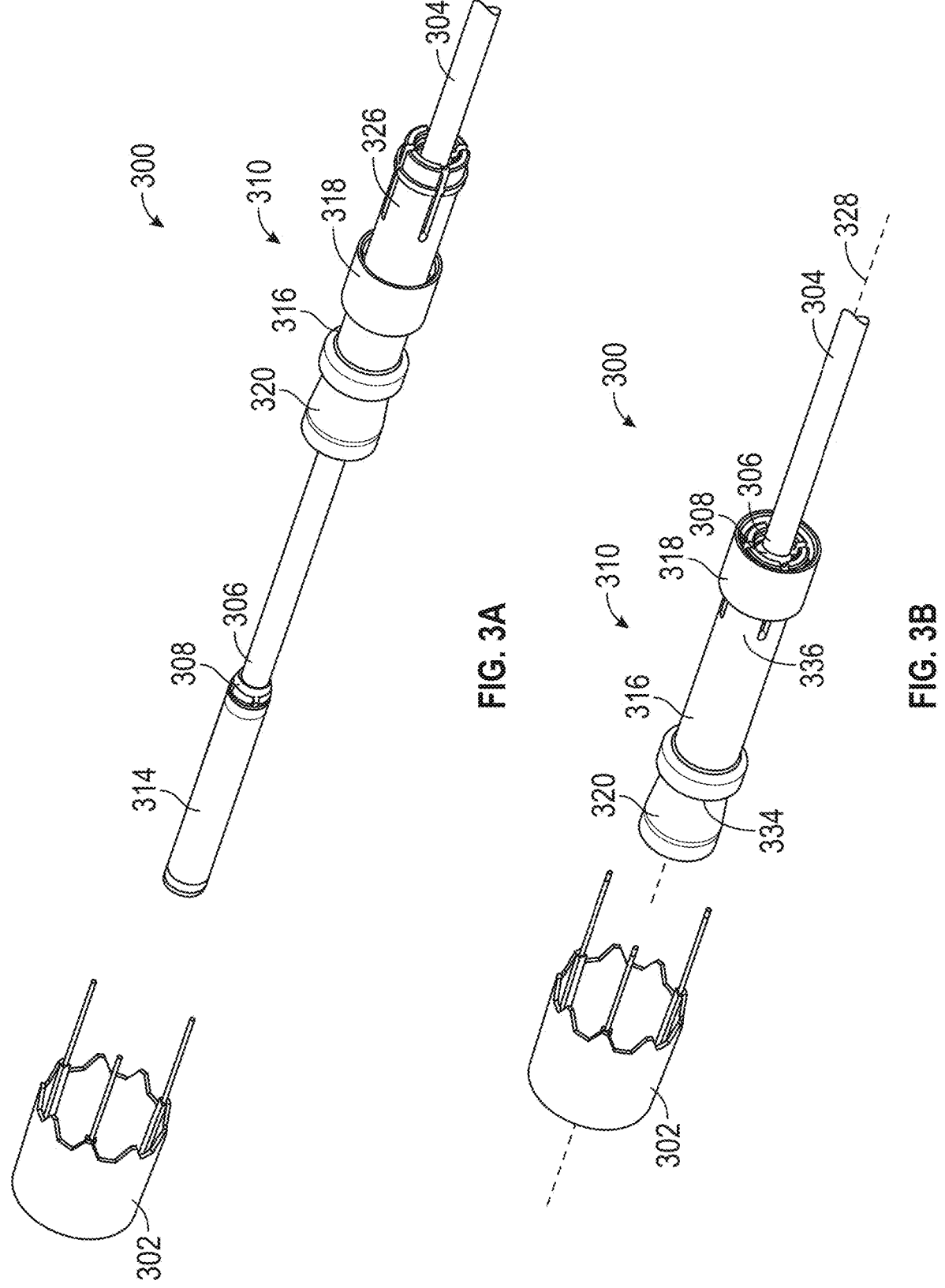
FIG. 3A is a perspective view of a system for loading a prosthetic medical device, such as a prosthetic heart valve, into a delivery apparatus, a loading assembly of the system shown disengaged from the delivery apparatus.
FIG. 3B is a perspective view of the system of FIG. 3A showing the loading assembly engaged with a coupling of the delivery apparatus.

FIGS. 3A and 3B show a system 300 for loading a prosthetic medical device, such as a prosthetic heart valve 302, into a delivery apparatus (which may be similar to the delivery apparatus 100 of FIG. 1) which can comprise an elongated shaft 304 (which may be the same or similar to the shaft 107 of FIG. 1). A distal end portion 306 of the shaft 304 is shown in FIGS. 3A and 3B with a coupling 308 mounted on the distal end portion 306 of the shaft 304 and a delivery capsule 314 coupled to coupling 308 (FIG. 3A). In this way, the coupling 308 can join the delivery capsule 314 and the distal end portion 306 of the shaft 304 of the delivery apparatus to one another.

In some examples, the coupling 308 can comprise a rigid material that is more rigid than a material of the distal end portion 306 of the shaft 304. In some examples the coupling 308 can comprise a material that is more rigid than both the material of the distal end portion 306 of the shaft 304 and the delivery capsule 314.

As shown in FIGS. 3A and 3B, the system 300 can include the distal end portion 306 of the shaft 304 of the delivery apparatus, the coupling 308, and a loading assembly 310. The loading assembly 310 can be configured to securely attach to the coupling 308, as described in more detail below. In some examples, the system 300 can further include the prosthetic heart valve 302 (or another prosthetic medical device, such as a stent) in an at least partially radially expanded configuration, outside of (exterior to) the delivery capsule 314.

FIG. 3A shows the system 300 in an uncoupled configuration where the loading assembly 310 is positioned away from and not coupled to the coupling 308. FIG. 3B shows the system 300 in a coupled configuration where the loading assembly 310 is coupled to the coupling 308 and the delivery capsule 314 is arranged within an interior of a portion of the loading assembly 310 (as shown in FIGS. 7, 8, and 12A-12C, as described further below).

Figures 12A, 12B, 12C:
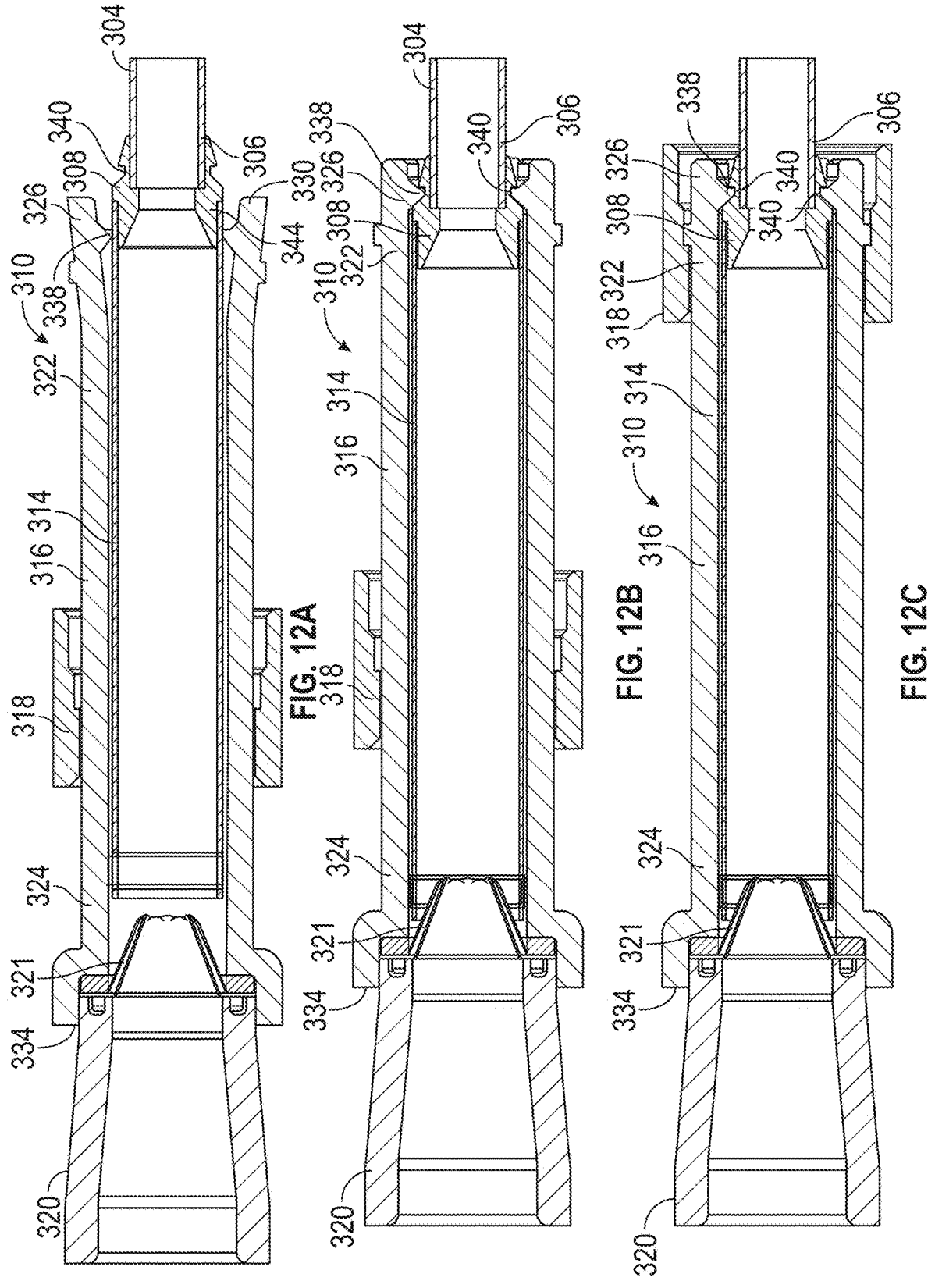
FIG. 12A is a side, cross-sectional view of the loading assembly of FIG. 4 surrounding a delivery capsule and portion of a coupling of the delivery apparatus, prior to engagement with the coupling.
FIG. 12B is a side, cross-sectional view of the loading assembly of FIG. 4 coupled to the coupling and a collar of the loading assembly in an unlocked configuration.
FIG. 12C a side, cross-sectional view of the loading assembly of FIG. 4 coupled to the coupling and the collar moved into a locked configuration where the collar holds a loading capsule of the loading assembly in locking engagement with the coupling.

The loading assembly 310 can comprise a loading capsule 316 (which can also be referred to as a loading sleeve or tube) and a collar 318 (FIGS. 3A and 3B). In some examples, the loading assembly 310 can further comprise a loader 320 which can, in some examples, have a slightly tapered inner lumen to facilitate loading of the prosthetic heart valve 302 into the delivery capsule 314. In some examples, the loader 320 can comprise a tapered portion 321 configured to further radially compress the prosthetic heart valve 302 as it moves through the tapered portion 321 (FIGS. 12A-12C). In some examples, the tapered portions 321 can be configured similarly to the tapered portion 728 shown in FIGS. 17-24, as described further below.

As explained further below and shown in FIGS. 6-8 and 12A-12C, the delivery capsule 314 can be coupled to a distal end of the coupling 308 and the loading capsule 316 can surround the delivery capsule 314 when the loading capsule 316 is coupled to the coupling 308, thereby positioning the loader 320 adjacent to a distal end of the delivery capsule 314 and a narrowed portion of the tapered portion 321 of the loader 320 inside the distal end of the delivery capsule 314 (FIGS. 12B and 12C). As such, the prosthetic heart valve 302 can be easily loaded into the delivery capsule 314 using the loading assembly 310.

FIGS. 4-8 show an example of a connection (or coupling) interface between a distal end portion of a delivery apparatus and the loading assembly 310. More specifically, FIGS. 4-8 show the loading assembly 310 coupled to the coupling 308 mounted on the distal end portion 306 of the shaft 304 of the delivery apparatus and in both an unlocked configuration (FIG. 4) and a locked configuration (FIGS. 5-8). In the unlocked configuration (FIG. 4) of the loading assembly 310, the collar 318 can be disengaged from a proximal end portion 322 of the loading capsule 316 (a disengaged position of the collar 318) and in the locked configuration (FIGS. 5-8) of the loading assembly 310, the collar 318 can be engaged with the proximal end portion 322 of the loading capsule 316 (an engaged position of the collar 318).

Figure 4:
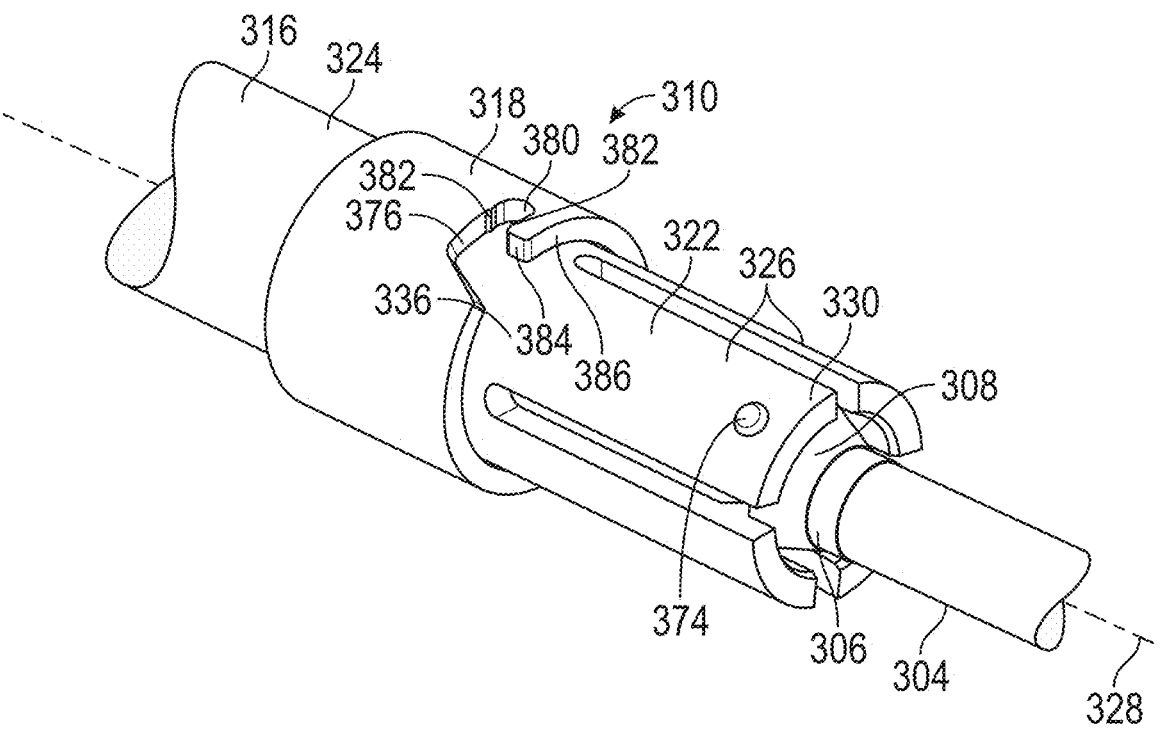
FIG. 4 is a perspective view of an example of a loading assembly coupled to a coupling mounted on a distal end portion of a delivery apparatus, the loading assembly in an unlocked configuration where a collar of the loading assembly is disengaged from a loading capsule of the loading assembly.

The loading capsule 316 can comprise a distal end portion (or first portion) 324 and the proximal end portion (or second portion) 322. As shown in FIG. 4, the proximal end portion 322 can comprise a plurality of axially extending flexible members (or fingers) 326 (relative to a central longitudinal axis 328 of the system 300, which can also be a central longitudinal axis of the loading assembly 310 and the shaft 304 of the delivery apparatus). The flexible members 326 are spaced apart from one another around a circumference of the proximal end portion 322 and can be configured to flex radially outward from the distal end portion 324, relative to the central longitudinal axis 328.

In some examples, the flexible members 326 can comprise a flexible polymeric or metal material such that proximal, free end portions 330 of the flexible members 326 are configured to flex or bend radially outward (from the distal end portion 324) in response to a radially outward pressure (or force) against inner surfaces 332 of the flexible members 326 (FIGS. 7 and 8) and then may return to the axially extending orientation (as shown in FIGS. 4-8) or a slightly radially inward biased orientation when the radially outward pressure is removed.

In some examples, an entirety of the loading capsule 316 can comprise the same material. In other examples, the flexible members 326 can comprise a more flexible material than the distal end portion 324 of the loading capsule 316. In some examples, the flexible members 326 can comprise a relatively rigid polymeric or metal material, but may be configured to flex radially outward and/or inward due to a selected thickness of the flexible members 326 and/or due to the flexible members 326 being spaced apart from one another by elongate gaps, spaces, or slots 325 (FIG. 6) in the proximal end portion 322.

The distal end portion 324 of the loading capsule 316 can be annular and continuous around its circumference (without any flexible members). Further, the distal end portion 324 can extend from a distal end 334 of the loading capsule 316 (FIG. 3) to attached ends 336 of the flexible member 326 (FIGS. 3B-6).

Figures 6, 7, 8:
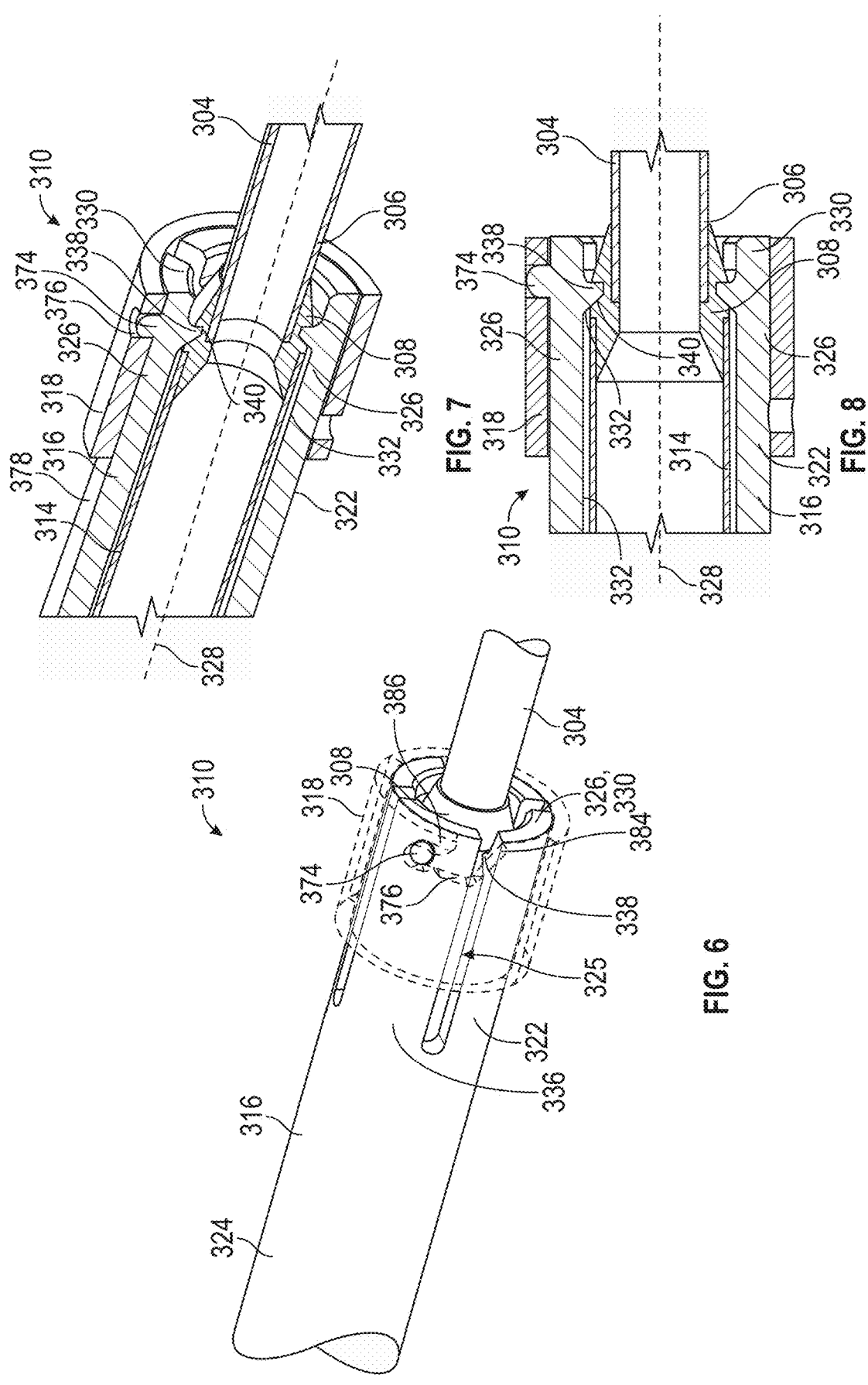
FIG. 6 is another perspective view of the loading assembly of FIG. 5 in the locked configuration illustrating the collar as transparent to show the underlying flexible members of the loading capsule.
FIG. 7 is a perspective, cross-sectional view of the loading assembly of FIG. 5, in the locked configuration.
FIG. 8 is a side, cross-sectional view of the loading assembly of FIG. 5, in the locked configuration.

One or more of the flexible members 326 can include a protrusion (inner protrusion or projection) 338 that extends outward from the inner surface 332 of the flexible member 326 and radially inward toward the central longitudinal axis 328 (FIGS. 7 and 8). In some examples, each flexible member 326 can include a protrusion 338. The protrusions 338 can be referred to herein as mating features and/or radial protrusions.

In some examples, as shown in FIGS. 3A and 4-8, the loading capsule 316 can comprise four flexible members 326 and four protrusions 338 (one protrusion 338 for each flexible member 326). However, in other examples, the loading capsule 316 can include more or less than four flexible members 326 and four protrusions 338 (e.g., two, three, six, or the like). In still other examples, only a portion of the flexible members 326 can include a protrusion 338 (e.g., two or three).

The protrusions 338 of the flexible members 326 are configured to engage and couple to complementary mating features in the coupling 308. In some examples, as shown in FIGS. 7-10, the complementary mating features of the coupling 308 are one or more depressions, grooves, slots, or channels 340 that are depressed into an outer surface (radially outward facing surface) 342 of the coupling 308 (FIGS. 9A-10).

FIGS. 9A and 9B, 10, and 11 show perspective views, a side view, and a cross-sectional view (taken along the section 11-11 in FIG. 10 between adjacent channels 340), respectively, of an exemplary example of the coupling 308 not attached to the delivery apparatus. FIGS. 7 and 8 show cross-sectional views of the coupling 308 mounted to the distal end portion 306 of the shaft 304, showing a cross-section of two oppositely arranged channels 340.

In some examples, as shown in FIGS. 7-10, the coupling 308 can comprise four discrete (separate) channels 340 (e.g., each one configured to receive the protrusion 338 of a corresponding one of the flexible members 326) spaced apart from one another around a circumference of the coupling 308. In some examples, the coupling 308 can comprise less than four discrete channels 340, such as two or three discrete channels 340. In other examples, the coupling 308 can comprise one continuous annular channel 340 around a circumference of the coupling 308 configured to receive all the protrusions 338.

In some examples, as shown in FIGS. 9A-11, the coupling 308 can comprise a first portion 344 (which may be a distal portion when the coupling 308 is mounted on/to the distal end portion 306 of the shaft 304, as shown in FIGS. 7, 8 and 12A-12C), a second portion 346, and a third portion 348 (which can be a proximal portion when mounted on the distal end portion 306 of the shaft 304), the second portion 346 disposed between the first portion 344 and the third portion 348. It should be noted that although the coupling 308 can be referred to as having these three portions, the coupling 308 can be formed as one piece (e.g., molded together as one piece).

The first portion 344 can be configured to couple to the delivery capsule 314. For example, the first portion 344 can comprise an annular outer surface 350 (FIGS. 9A-11) that is configured to receive a proximal end portion of the delivery capsule 314 thereon (as shown in FIGS. 7, 8, and 12A-12C). For example, a first outer diameter 352 of the first portion 344 can be the same or slightly smaller than an inner diameter of the delivery capsule 314. Thus, when the delivery capsule 314 is coupled to and around the first portion 344, the outer surface 350 and an inner surface of the delivery capsule 314 can have face-to-face (face-sharing) contact with one another.

In some examples, the coupling 308 can have a step (stepped transition) 354 (FIGS. 10 and 11) between the first portion 344 and the second portion 346 and the second portion 346 can have a second outer diameter 356 that is larger than the first outer diameter 352 (FIG. 11). The step 354 or difference between the first outer diameter 352 and the second outer diameter 356 can be selected such than when the delivery capsule 314 is coupled to the first portion 344, an outer surface of the delivery capsule 314 is flush with the outer surface 342 of the second portion 346 of the coupling 308.

As introduced above, the channels 340 are depressed into the outer surface 342 of the second portion 346, radially inward toward a central longitudinal axis of the coupling 308. A shape (including a depth, length, and cross-sectional profile) of each channel 340 can be selected based on and to fit a corresponding protrusion 338 of the loading capsule 316. For example, as shown in FIGS. 7-10 and 12A-12C, the protrusions 338 and channels 340 can have corresponding tapered or angled shapes (e.g., angled relative to the central longitudinal axis 328 at an angle between 45 and 90 degrees) that are configured to mate with one another. The angling or tapering of the channels 340 (FIGS. 9A-10), and corresponding angling or tapering of the protrusions 338 may enable to the protrusions 338 to more easily slide into the channels 340 as the loading capsule 316 is slid over the coupling 308 (as shown in FIGS. 12A and 12B, as described further below).

More specifically, as an example, each channel 340 can have an angled surface 358 (angled relative to the central longitudinal axis 328), a base surface 360 (parallel with the outer surface 342), and a normal surface 362 (normal to a direction parallel to the central longitudinal axis 328) (FIGS. 9A-10). Each protrusion 338 can have similar, corresponding surfaces.

The third portion 348 can be configured to couple to the distal end portion 306 of the shaft 304 (FIGS. 7, 8, and 12A-12C). As shown in FIGS. 9A-11, the third portion 348 can have a tapered outer surface 364 that tapers from the second outer diameter 356 (at an interface between the second portion 346 and the third portion 348) to a third inner diameter 366 of the third portion 348, at a proximal end 388 of the coupling 308 (FIG. 11).

In some examples, the third inner diameter 366 can be constant along a length of the third portion 348 and shaped to receive the distal end portion 306 of the shaft 304 (e.g., the same size or slightly larger than an outer diameter of the shaft 304). The second portion 346 can have a second inner diameter 368 which is smaller than the third inner diameter 366. In some examples, the second inner diameter 368 can be an innermost diameter of the second portion 346 that is defined by a depth of the channels 340 and the base surface 360.

In some examples, the first portion 344 can have an inner surface 370 that tapers from the first outer diameter 352, at a distal end 372 of the coupling 308, to the second inner diameter 368 (FIG. 11).

Returning to FIGS. 4-8, an interface between the loading capsule 316 and the collar 318 is shown. The collar 318 is configured to slide over the flexible members 326 of the loading capsule 316 after the loading capsule 316 is engaged with the coupling 308 (FIGS. 5-8 and 12B-12C) and prevent the flexible members 326 from flexing radially outward, thereby maintaining the flexible member 326 engaged with the coupling 308 (and maintaining the loading capsule 316 securely engaged with and coupled to the coupling 308, and thus, the distal end portion of the delivery apparatus).

For example, in some instances (as shown in FIGS. 4-8), the loading capsule 316 can comprise one or more locking features, configured as outer protrusions (or projection) 374 in FIGS. 4-8, and the collar 318 can comprise one or more complementary locking features, configured as slots 376 in FIGS. 4-8, each slot 376 configured to mate with (in locking engagement) a corresponding one of the one of the outer protrusions 374. In some examples, the loading assembly 310 can comprise two pairs of outer protrusions 374 and slots 376. For example, the collar 318 can comprise two slots 376 spaced apart from one another on radially opposite sides of the collar 318 (e.g., 180 degrees apart) and the loading capsule 316 can comprise two outer protrusions 374 spaced apart from one another on radially opposite sides of the loading capsule 316 (e.g., 180 degrees apart).

In other examples, the loading assembly may only include one outer protrusion 374 and one slot 376 configured to mate with one another. In still other examples, the loading assembly can comprise more than two outer protrusions 374 and slots 376 (e.g., three or four).

Each outer protrusion 374 can be disposed on one of the flexible members 326, proximate to or at the free end portion 330 of the flexible member 326. For example, in the instance shown in FIGS. 4-8, two of the flexible members 326 that are disposed on opposite sides of the loading capsule 316 can each include one of the protrusions 374 on the free end portion 330. In some examples, as shown in FIGS. 7 and 8, each outer protrusion 374 can protrude radially outward from an outer surface 378 of the corresponding flexible member 326 and the protrusion (inner protrusion) 338 can protrude outward, in a radially inward direction, from the inner surface 332 of the corresponding flexible member 326 in an opposite direction than the outer protrusion 374. Said another way, the outer protrusion 374 can extend radially outward relative to (away from) the central longitudinal axis 328 and the protrusion 338 can extend radially inward relative to (toward) the central longitudinal axis 328.

In some examples, as shown in FIGS. 4-8, the outer protrusion 374 can be configured as a dome-shaped peg. In other examples, the outer protrusion can have a different protruding shape, such as a square, oval, hexagon, or the like.

Figure 5:
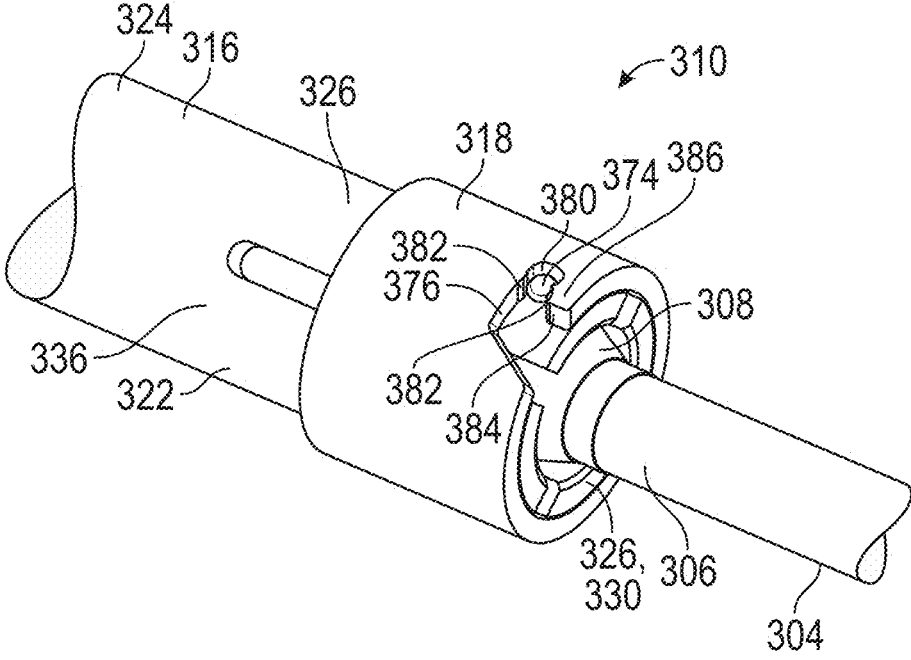
FIG. 5 is a perspective view of the loading assembly of FIG. 4 coupled to the coupling and in a locked configuration where the collar is engaged with the loading capsule.

Each slot 376 can be configured to initially axially engage the corresponding outer protrusion 374, through an open end 384 of the slot 376 and allow rotation of the collar 318 to the engaged position where the outer protrusion 374 is held in place at a closed end 380 of the slot 376 by two retaining features (e.g., detents or protruding member) 382 of the slot 376 (FIGS. 4-6). Each slot 376 can further comprise a cantilevered extension portion 386 that is configured to pivot or deflect (in an axial direction) to allow the outer protrusion 374 to pass through the two retaining features 382. The extension portion 386 can include one of the two retaining features 382.

For example, as the collar 318 slides toward the outer protrusions 374, each outer protrusion 374 is initially engaged by and passes through the open end 384 of the corresponding slot 376. The outer protrusion 374 then slides axially inward into the slot 376 and then radially toward the closed end 380 of the slot 376 as the collar 318 rotates. The extension portion 386 of the slot 376 can then deflect (e.g., elastically outward) as the collar 318 rotates further and the outer protrusion 374 is pushed through the retaining features 382 and to the closed end 380 of the slot 376. The extension portion 386 can then return (snap back) into place, the retaining features 382 thereby holding the outer protrusion 374 in place within the slot 376. As a result, the flexible members 326 of the loading capsule 316 are locked in engagement with the coupling 308, thereby providing a secure (but removable) coupling between the coupling 308 and the loading assembly 310.

FIGS. 12A-12B illustrate an exemplary method for coupling the loading assembly 310 to the coupling 308 and locking the loading assembly 310 in engagement with the coupling 308 such that the loading capsule 316 cannot be inadvertently uncoupled from the coupling 308. Specifically, FIG. 12A shows the loading assembly 310 uncoupled from the coupling 308, where the protrusions 338 of the loading capsule 316 are not engaged with the corresponding channels 340 in the coupling 308. In FIG. 12A, the free end portions 330 of the flexible members 326 of the loading capsule 316 (which include the protrusions 338) have been moved (slid) over and into contact with the first portion 344 of the coupling 308. As a result, the flexible members 326 are bent radially outward (FIG. 12A).

As shown in FIG. 12B, the loading capsule has been moved further over the coupling 308 until the protrusions 338 are positioned over (around) the channels 340 of the coupling 308. As a result, the protrusions 338 on the flexible members 326 extend into and mate with the channels 340, thereby allowing the flexible members 326 to bend radially inward, back into their resting position. As a result, the loading capsule 316 is coupled to the coupling 308, but the loading assembly is still in the unlocked configuration (the collar 318 is positioned away from the flexible members 326, as shown in FIG. 12B). Thus, it may be possible for the flexible members to bend back radially outward and disengage from the coupling 308.

The collar 318 can then be moved over the flexible members 326 and rotated into the engaged and locked configuration, as shown in FIG. 12C. In this configuration, the slots 376 of the collar 318 engage the outer protrusions 374 of the flexible members 326, as described above with reference to FIGS. 4-8. As a result, the collar 318 is held in place over the flexible members 326 and the flexible members 326 are held in locking engagement with the coupling 308. As a result, the loading assembly 310 is securely coupled to the coupling 308 and a prosthetic medical device (e.g., prosthetic heart valve) can be loaded into the delivery capsule 314 with the loading assembly 310 (e.g., through the loader 320). For example, the prosthetic medical device can be inserted into the open distal end of the loader 320 and pushed and/or pulled through the loader 320, including the tapered portion 321 of the loader 320, and into the delivery capsule 314. As the prosthetic medical device passes through the loader 320, and in particular the tapered portion 321 of the loader 320, it becomes radially compressed to a smaller diameter such that it can be received within the delivery capsule 314.

Figure 13:
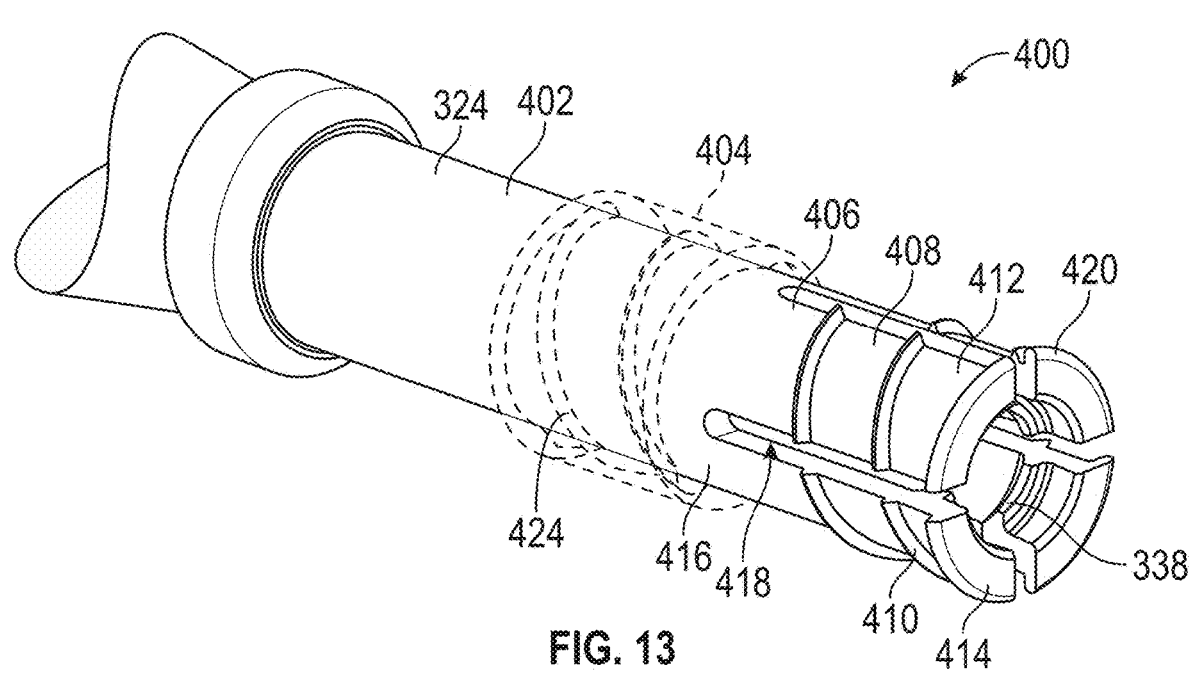
FIG. 13 is a perspective view of another example of a loading assembly configured to couple to and be held in locking engagement with a coupling mounted on a distal end portion of a delivery apparatus.
Figure 14:
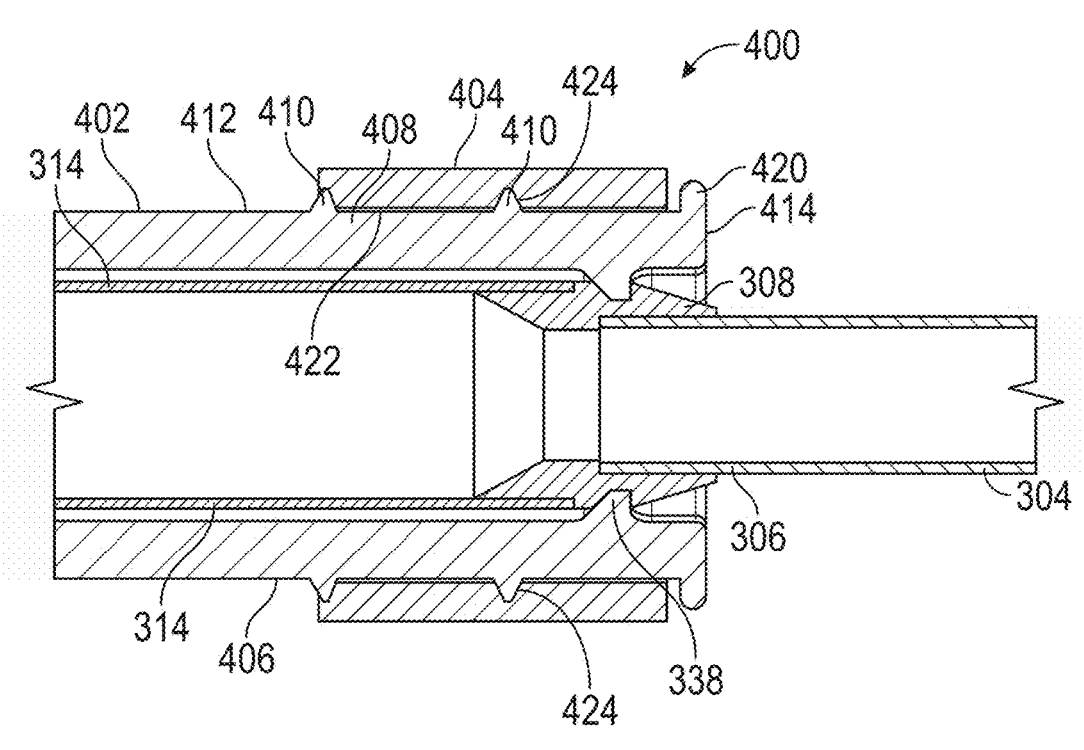
FIG. 14 is a side, cross-sectional view of the loading assembly of FIG. 13, coupled to the coupling and in a locked configuration.

FIGS. 13 and 14 show another example of a locking interface between a loading capsule 402 and a collar 404 of a loading assembly 400. The loading assembly 400 can be the same or similar to the loading assembly 310 of FIGS. 3A-8, except for the locking interface between (and locking features of) the loading capsule 402 and the collar 404. For example, the loading capsule 402 can include a proximal end portion 406 comprising a plurality of flexible members 408 (similar to the flexible members 326 shown in FIGS. 3A-8) that each include an inner protrusion 338 and are configured to flex radially outward. However, instead of the outer protrusions 374, the proximal end portion 406 can comprise a helical thread (or protrusion or ridge) 410 extending across an outer surface 412 of the flexible members 408, from free (proximal) ends 414 of the flexible members 408 toward (or in some examples, to) attached ends 416 of the flexible members (e.g., ends that are attached to the distal end portion 324 of the loading capsule 402). The thread 410 can be discontinuous around a circumference of the proximal end portion 406 such that the thread 410 extends along a defined helical path from one flexible member 408 to an adjacent flexible member 408, but without extending across a space (or gap or slot) 418 between adjacent flexible members 408.

In some examples, the free ends 414 of the flexible members 408 can each comprise a lip or radial extension portion 420 which extends radially outward from the outer surface 412. In some examples, the radial extension portions 420 can serve as a stop for the collar 404 (to prevent the collar from traveling further axially in the proximal direction), as explained further below.

The collar 404 can have an inner surface (radially inward facing inner surface) 422 (shown in FIG. 14) comprising a helical groove (thread) 424 depressed into the inner surface 422 (FIGS. 13 and 14). The helical groove 424 is complementary to (e.g., with the same lead and pitch) and configured to mate with the helical thread 410 of the flexible members 408. The helical groove 424 can extend along an axial length of the collar 404.

FIG. 13 shows the collar 404 in the disengaged and unlocked configuration where it is spaced axially away from the flexible members 408. During use, after the flexible members 408 engage the coupling 308 (similar to as shown in FIG. 12B and as shown in FIG. 14), the collar 404 can be moved axially, in the proximal direction, to the proximal end portion 406 of the loading capsule 402 and rotated until the helical groove 424 engages the thread 410 of the flexible members 408. The collar 404 can then be further rotated such that it moves axially over and is threaded onto the flexible members 408, until the collar 404 is positioned adjacent to and/or hits the radial extension portions 420 (FIG. 14). In this position (the engaged or locked configuration) the collar 404 can be securely engaged with the flexible members 408 and lock the flexible members 408 in engagement with the coupling 308, thereby securely coupling the loading assembly 400 to the coupling 308 and the distal end portion of the delivery apparatus (FIG. 14).

Figure 15:
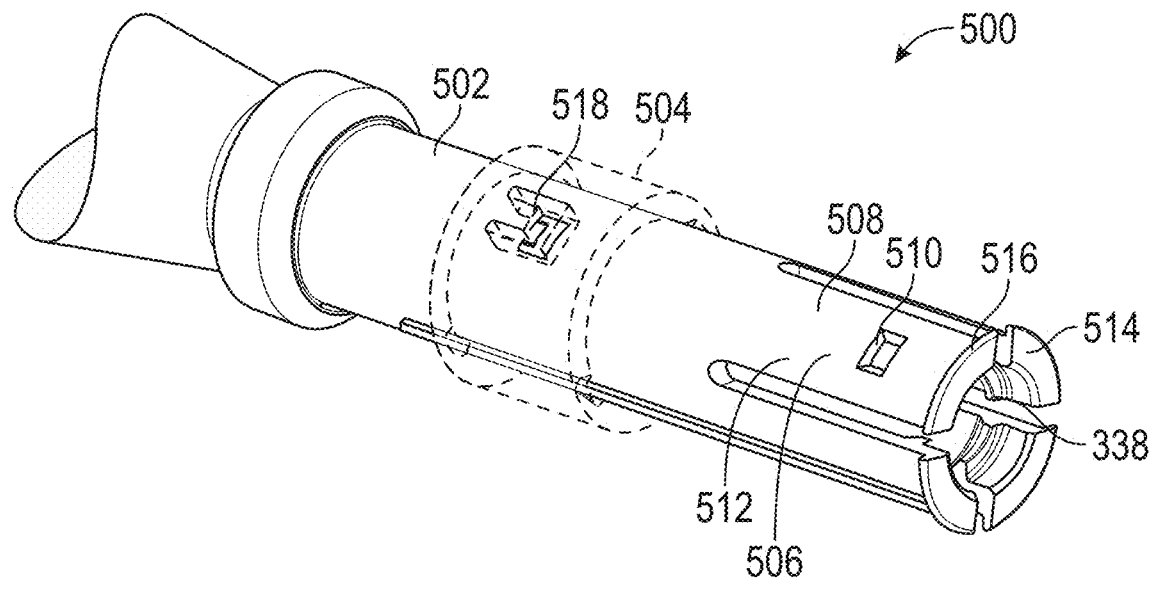
FIG. 15 is a perspective view of another example of a loading assembly configured to couple to and be held in locking engagement with a coupling mounted on a distal end portion of a delivery apparatus.

FIG. 15 shows another example of a locking interface (in a disengaged or unlocked configuration) between a loading capsule 502 and a collar 504 of a loading assembly 500. The loading assembly 500 can be the same or similar to the loading assembly 310 of FIGS. 3A-8, except for the locking interface between (and locking features of) the loading capsule 502 and the collar 504. For example, the loading capsule 502 can include a proximal end portion 506 comprising a plurality of flexible members 508 (similar to the flexible members 326 shown in FIGS. 3A-8) that each include an inner protrusion 338 and are configured to flex radially outward. However, instead of the outer protrusions 374, the proximal end portion 506 can comprise an engagement channel or slot 510 disposed in one of the flexible members 508. The slot 510 can extend (or be depressed) into an outer surface 512 of the flexible member 508. In some examples, the slot 510 can extend entirely through a thickness of the flexible member 508 (from the outer surface 512 to an inner surface of the flexible member 508).

Similar to the flexible members 408, in some examples (as shown in FIG. 15), free ends 514 of the flexible members 508 can each comprise a lip or radial extension portion 516 which extends radially outward from the outer surface 512. In some examples, the radial extension portions 516 can serve as a stop for the collar 504 (to prevent the collar from traveling further axially in the proximal direction).

As shown in FIG. 15, the collar 504 can comprise a mating projection (which can be configured as a tab) 518 that is configured to engage (and lock into) the corresponding slot 510 when the collar 504 is moved over the flexible members 508. For example, the projection 518 can be disposed on an inner surface of the collar 504 and be configured to extend radially into the slot 510 when moved over the slot 510, thereby locking the collar 504 to the flexible members 508.

In some examples, more than one of the flexible members 508 can include a slot 510 and the collar 504 can comprise a plurality of projections 518, each configured to engage with a corresponding slot of a plurality of slots 510. For example, in some examples, two opposing flexible members 508 can each include a slot 510 and the collar 504 can include two projections 518 spaced approximately 180 degrees apart from one another on the collar 504.

In this way, an inner surface of a collar of a loading assembly can comprise a first mating element or locking feature (e.g., slot 376, helical groove 424, or projection 518) configured to mate with and couple to a complementary second mating element or locking feature on an outer surface of one or more flexible members of a loading capsule of the loading assembly (e.g., outer protrusion 374, helical thread 410, or slot 510). As a result, the collar can be moved into an engaged and locked configuration where the flexible members are locked in engagement with the coupling (such that they cannot flex radially outward and become uncoupled from the coupling).

Figure 16:
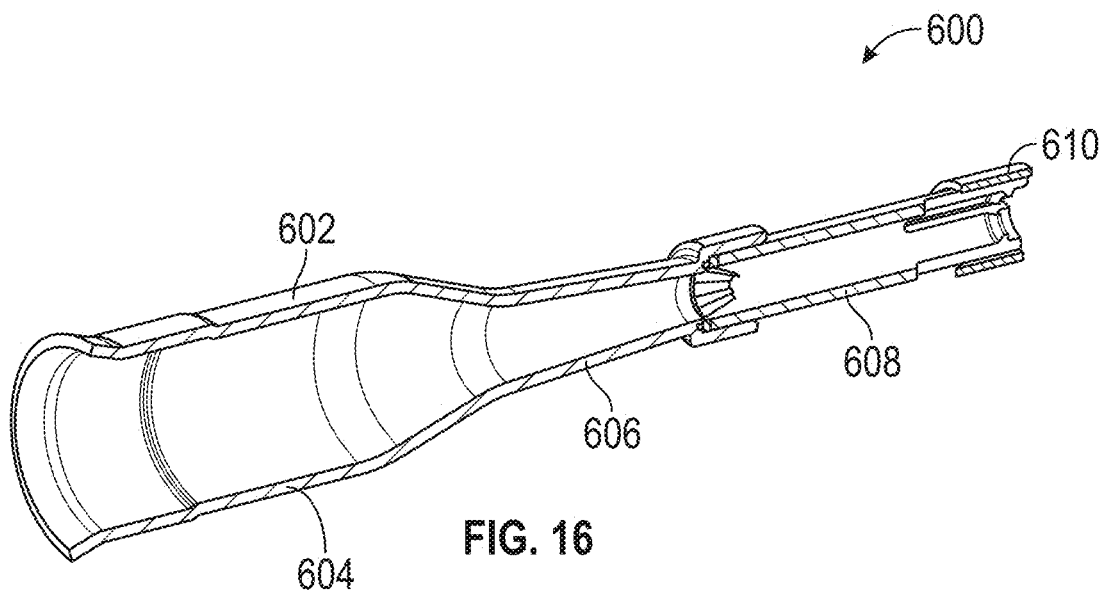
FIG. 16 is a perspective, cross-sectional view of an example of a loader for a loading assembly which comprises an integrated device housing configured to receive an at least partially radially expanded prosthetic medical device.

Turning now to FIG. 16, an example of a loader 602 for a loading assembly 600 which includes an integrated device (or valve) housing is shown. In some examples, a device, such as a prosthetic heart valve (e.g., prosthetic heart valve 200 of FIG. 2) that is in an at least partially radially expanded state can be attached to a delivery apparatus (e.g., delivery apparatus 100 of FIG. 1) after manufacturing and prior to an implantation procedure. In such cases, the prosthetic heart valve is packaged and transported (e.g., shipped) with the delivery apparatus to a medical facility where it will be implanted. Thus, it is desirable to shield and protect the prosthetic heart valve (in the radially or at least partially radially expanded state) prior to implantation (in the manufacturing facility, during shipping, and during any shelf life prior to implantation).

As shown in FIG. 16, the loader 602 can comprise a device housing portion 604 configured to surround and house the radially expanded prosthetic heart valve (or other prosthetic medical device, such as a stent) and a loading portion 606 that is configured to help load the prosthetic heart valve into a delivery capsule of the delivery apparatus. As shown in FIG. 16, the loader 602 can be directly coupled to a loading capsule 608 of the loading assembly 600, which can be similar to the loading capsule 316 of FIGS. 3A-8. The loading assembly 600 can further include a collar 610 (which can be similar to collar 318 of FIGS. 3A-8).

However, when the loader 602 including the device housing portion 604 is fixed to the loading capsule 608, as shown in FIG. 16, it may be difficult to radially compress the prosthetic heart valve and load it into the delivery capsule in the radially compressed state. For example, if the prosthetic heart valve needs to be crimped with a crimping device, the configuration of the loader 602 makes it difficult or impossible to do so.

Thus, a device housing that is easily removable from a loading portion (configured to radially compresses and/or facilitate loading of a radially compressed device into the delivery capsule) of the loading assembly is desirable. As a result, a prosthetic heart valve or other medical device can be enclosed within and protected prior to an implantation procedure by the removable device housing but then radially compressed and loaded into the delivery capsule of the delivery apparatus by removing the removable device housing from a remainder of the loading assembly.

Figures 17, 18:
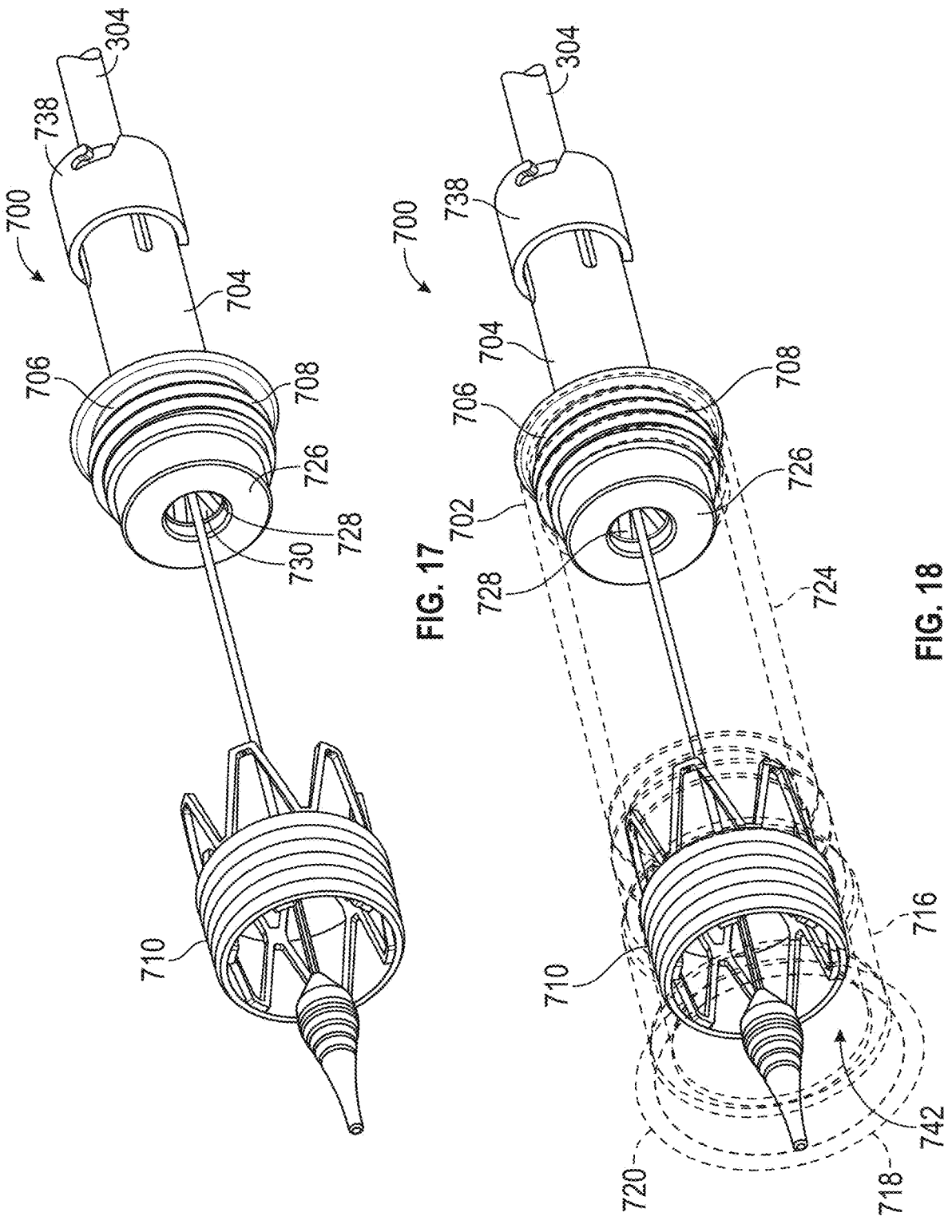
FIG. 17 is a perspective view of an example of a loading assembly including a detachable device housing that is removable from a remainder of the loading assembly, showing the device housing removed from a loading capsule of the loading assembly.
FIG. 18 is a perspective view of the loading assembly of FIG. 17 with the device housing attached to the loading capsule, illustrating the device housing in dashed lines to show a prosthetic heart valve contained within the device housing.
Figure 19:
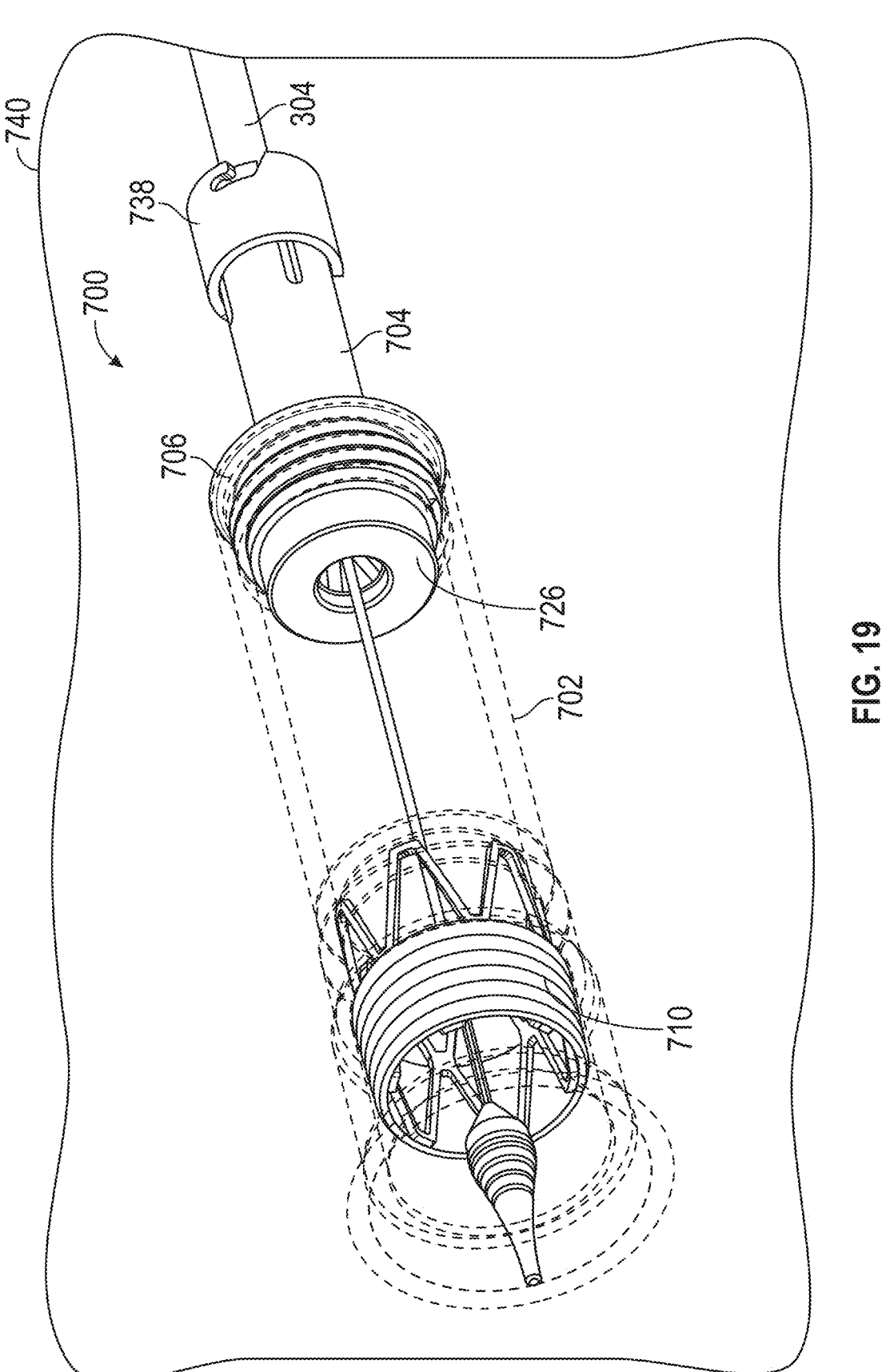
FIG. 19 is a perspective view of the loading assembly of FIG. 18 housing the prosthetic heart valve and contained within a sterile package.
Figures 20, 21:
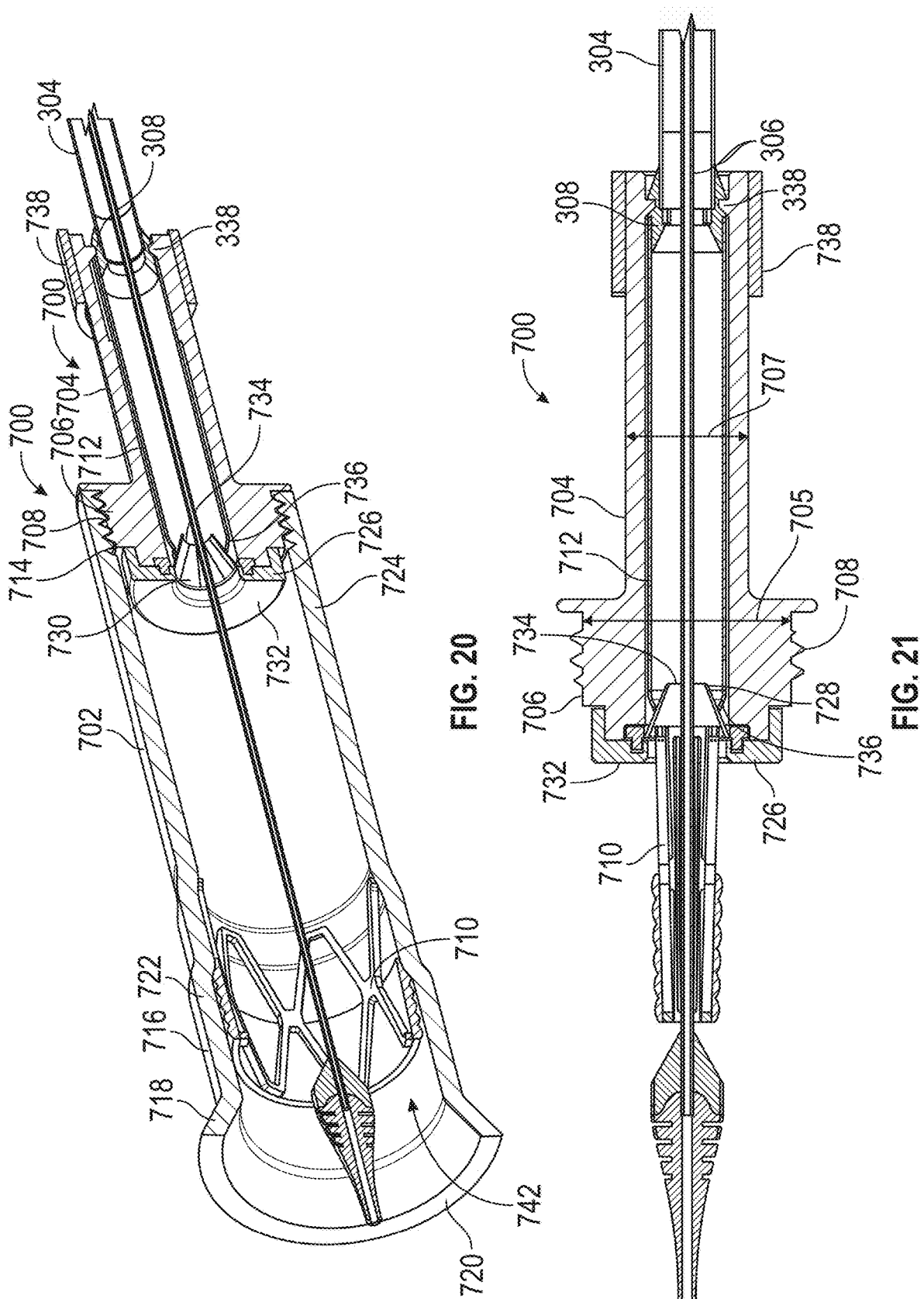
FIG. 20 is a perspective, cross-sectional view of the loading assembly of FIG. 18, showing the prosthetic heart valve contained within the device housing, the device housing attached to the loading capsule.
FIG. 21 is a side, cross-sectional view of the loading assembly of FIG. 17, showing the device housing removed from the loading capsule and the prosthetic heart valve radially compressed and ready to be loaded into a delivery capsule of a delivery apparatus to which the loading assembly is coupled.

FIGS. 17-21 show one example of a loading assembly 700 including a detachable device housing 702 (FIGS. 18-21) that is removable from (removably coupled to) a remainder of the loading assembly 700 (shown removed from the loading assembly 700 in FIGS. 17 and 21). FIGS. 18 and 19 show the device housing 702 in dashed lines (transparent) to show an underlying prosthetic heart valve 710 and portions of the delivery apparatus that it encloses when coupled to the remainder of the loading assembly 700 (e.g., the loading capsule, as explained further below).

The loading assembly 700 is shown attached to a distal end portion of a delivery apparatus (which may be the same or similar to the delivery apparatus 100 of FIG. 1). Specifically, the loading assembly 700 can include a loading capsule 704 coupled to the coupling 308 of the delivery apparatus that connects a delivery capsule 712 (which may be similar to the delivery capsule 314 of FIGS. 3A, 7, 8, and 12A-12C) to the distal end portion 306 of the shaft 304 (FIGS. 20 and 21). The loading capsule 704 can be configured similarly to the loading capsule 316 of FIGS. 3A-8 (or the loading capsule 402 of FIGS. 13 and 14 or loading capsule 502 of FIG. 15), except for its distal end portion 706 which comprises an attachment interface 708 (FIGS. 18, 20, and 21).

In some examples, the distal end portion 706 can have a larger diameter 705 that an outer diameter 707 of a proximal end portion of the loading capsule 704 (FIG. 21). Further, in some examples, as shown in FIGS. 17-21, the attachment interface 708 on the distal end portion 706 can comprise a plurality of threads configured to mate with complementary threads of an attachment interface 714 on the device housing 702 (threads of the attachment interface 714 are shown in FIG. 20).

In other examples, the attachment interface 708 can comprise a tab, snap, or other type of interlocking feature(s) configured to mate with and couple to complementary interlocking features of the attachment interface 714 on the device housing 702. In this way, the attachment interface 708 of the loading capsule 704 and the attachment interface 714 of the device housing 702 are configured to removably couple the device housing 702 to the loading capsule 704 such that the prosthetic heart valve 710 (or other prosthetic medical device) can be enclosed and protected within the device housing 702 prior to an implantation procedure (as shown in the cross-sectional view of FIG. 20). Then, the device housing 702 can be easily detached from the loading capsule 704 (as shown in the cross-sectional view of FIG. 21) in order to radially compress (e.g., with a crimping device) the prosthetic heart valve 710 and load it with the loading assembly 700 into the delivery capsule 712.

For example, FIGS. 20 and 21 show cross-sectional views of the loading assembly 700 with the device housing 702 attached to the loading capsule 704 (the attachment interface 708 and attachment interface 714 engaged with one another) (FIG. 20) and the device housing 702 detached from the loading capsule (FIG. 21). As shown in FIG. 20, the device housing 702 can be annular and further comprise a distal end portion 716 forming an inner cavity 742 configured to receive and hold therein the prosthetic heart valve 710 (or other prosthetic medical device). For example, the distal end portion 716 can have a first portion 718 disposed at a distal end 720 of the device housing 702 that is wider than a remainder of the device housing 702 such that the prosthetic heart valve 710 in a radially expanded state can be inserted into the device housing 702. In some examples, as shown in FIG. 20, the first portion 718 can taper radially inward to a second portion 722 of the distal end portion 716 which is shaped to receive and hold therein the at least partially radially expanded prosthetic heart valve 710. In some examples, the second portion 722 can have one or more stepped portions that narrow in diameter to a smaller diameter of a proximal end portion 724 of the device housing 702. The proximal end portion 724 can include the attachment interface 714 at its proximal end.

In some examples, when arranged within the device housing 702 (FIG. 20) the prosthetic heart valve 710 can be attached to the delivery apparatus by one or more actuator members 242 of the prosthetic valve and/or separate attachment members (e.g., cables, sutures, tethers, or the like).

In some examples, as shown in FIG. 18, the device housing 702 is annular and one continuous piece around its circumference. In other examples, such as those shown in FIGS. 25-28 (as described in further detail below), the device housing can instead be comprised of multiple pieces (shells) that are configured to form an annular shell together, but also be separated from one another.

In FIG. 21, the prosthetic heart valve 710 has been radially compressed and can be pushed and loaded into the delivery capsule 712. To facilitate this loading, the loading assembly 700 can comprise a loader (or loading element) 726 that is coupled to the distal end portion 706 of the loading capsule 704 and is configured to further radially compressed and/or load the radially compressed prosthetic heart valve 710 into the delivery capsule 712 (FIGS. 17-21). For example, the loader 726 can comprise a tapered portion 728 (FIGS. 17-21) that comprises a plurality of petals (wedge-shaped petals or tapered wedges) 730 (FIGS. 17 and 20). As explained further below with reference to the example of FIGS. 23 and 24, these petals 730 extend radially inward from a base or attached end 732 of the loader 726 that couples to the loading capsule 704 toward a proximal end of the loading capsule 704. Narrowed, free ends 734 of the petals 730 are configured to extend into the delivery capsule 712 such that a distal end portion 736 of the delivery capsule 712 surrounds the petals 730 (as shown in FIGS. 20 and 21). Since the distal end portion 736 of the delivery capsule 712 can taper radially inward and be relatively soft (e.g., softer than the prosthetic heart valve 710 and/or a remaining portion of the delivery capsule 712), the configuration of the petals 730 can protect the softer tip or distal end portion 736 of the delivery capsule 712 from being compressed or degraded during loading of the radially compressed prosthetic heart valve 710 into the delivery capsule 712.

For example, in some examples, the distal end portion 736 of the delivery capsule 712 can comprise a lower durometer polymeric material (e.g., PEBAX) and a remainder of the delivery capsule 712 can comprise a higher durometer polymeric material (e.g., Nylon).

As shown in FIGS. 17-21, the loading assembly 700 can further comprise a collar 738. In some examples, the collar 738 can be the same or similar to the collar 318 of FIGS. 3A-8 (or alternatively, the collar 404 of FIGS. 13 and 14 or the collar 504 of FIG. 15).

In some examples, as shown in FIG. 19, the loading assembly 700 with the at least partially radially expanded prosthetic heart valve 710 (or other prosthetic medical device) disposed inside the device housing 702 can be arranged and sealed within a sterile package 740 for shipping and/or storage until the prosthetic heart valve is ready to be implanted. The delivery apparatus to which the loading assembly 700 is coupled can also be arranged within the sterile package 740 (including shaft 304, as shown in FIG. 19).

In some examples, the prosthetic heart valve 710 can comprise a frame and a plurality of dry tissue leaflets attached the frame, where the dry tissue leaflets do not have to be stored in a hydrating solution (e.g., glutaraldehyde). Thus, in such examples, the sterile package 740 can be free of liquid (not filled with fluid). In some examples, together the sterile package 740, the loading assembly 700, the prosthetic heart valve 710 disposed within the device housing 702, and the delivery apparatus (or at least a portion of the delivery apparatus) can form a shipping assembly, wherein the loading assembly (with the prosthetic valve disposed therein) can be pre-assembled on the delivery apparatus. In other examples, the delivery apparatus can be contained in a separate sterile package apart from the loading the assembly and prosthetic valve.

Figures 22, 23, 24:
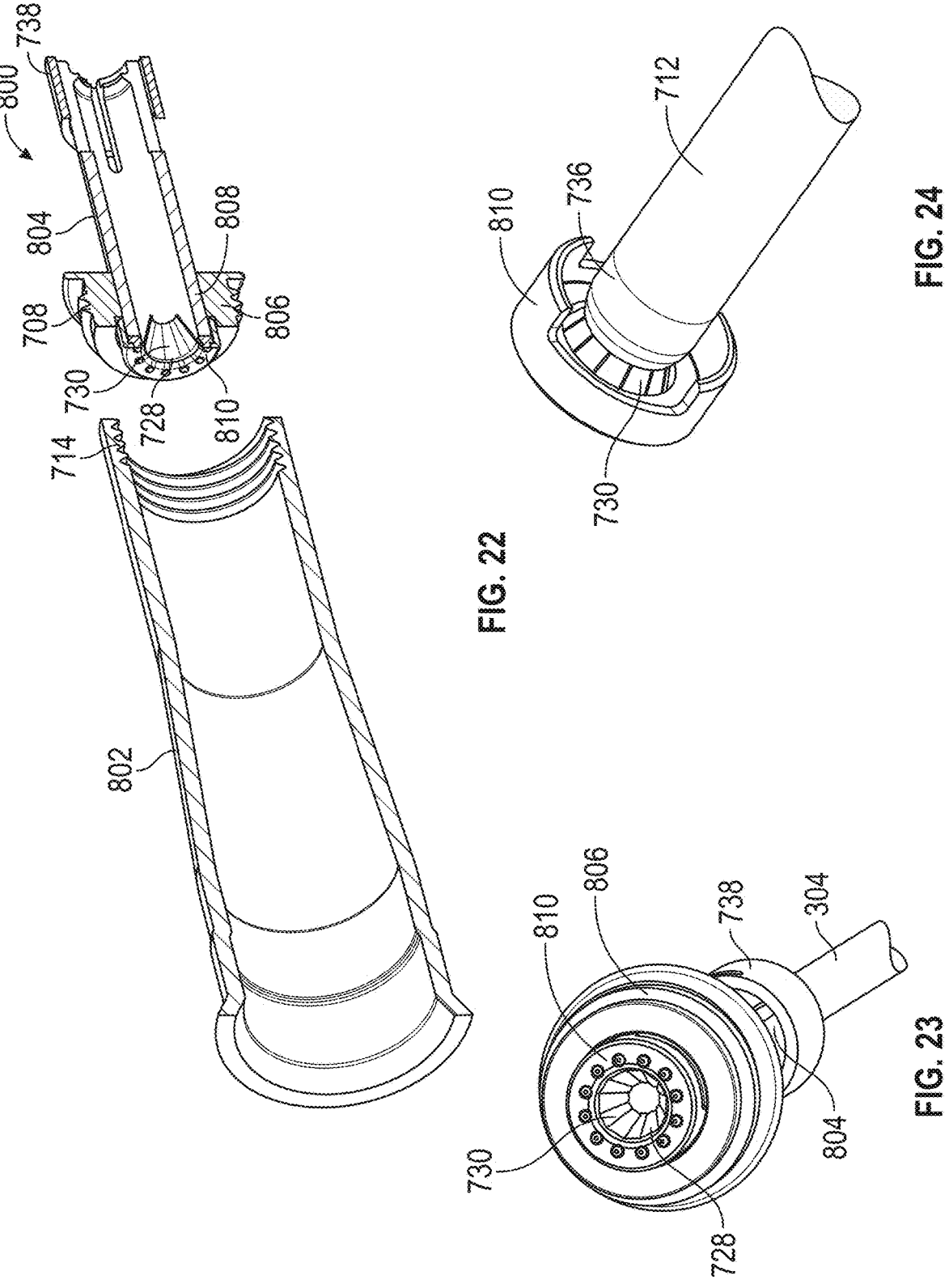
FIG. 22 is a perspective, cross-sectional view of another example of a loading assembly including a detachable device housing that is removable from a remainder of the loading assembly, the device housing shown detached from a coupling element coupled to an end of a loading capsule of the loading assembly.
FIG. 23 is an end, perspective view of a portion of the loading assembly of FIG. 22, showing a loader of the loading assembly.
FIG. 24 is another perceptive view of the portion of the loading assembly of FIG. 23, showing a delivery capsule interfacing with the loader.

FIGS. 22-24 show another example of a loading assembly 800 including a detachable device housing 802 (FIG. 22) that is removable from (removably coupled to) a remainder of the loading assembly 800 (shown removed from the loading assembly 800 in FIG. 23). The loading assembly 800 comprises a loading capsule 804, the device housing 802, a coupling (or attachment) element 806 comprising the attachment interface 708, a loader (or loading element) 810, and the collar 738. The device housing 802 can be removably coupled to the coupling element 806 which is attached to the loading capsule 804.

The loading assembly 800 can be similar to the loading assembly 700 of FIGS. 17-21, except the attachment interface 708 for mating with and coupling to the attachment interface 714 of the device housing 802 is on a separate part (the coupling element 806) instead of on the loading capsule 804. Thus, the loading capsule 804 of the loading assembly 800 can comprise a distal end portion 808 that couples to the loader 810 and the coupling element 806 can surround and be coupled to the distal end portion 808 of the loading capsule 804. The coupling element 806 comprises the attachment interface 708, as described above with reference to FIGS. 17-21.

In some examples, the device housing 802 can be the same or similar to the device housing 702 of FIGS. 17-21, but can comprise one or more stepped or tapered portions that decrease in diameter along its length (similar to the second portion 722 of the proximal end portion 716 of the device housing 702 shown in FIG. 20).

As shown in FIGS. 22-24, the loader 810 can be coupled to the distal end of the loading capsule 804 and comprises the tapered portion 728 that comprises the plurality of petals 730. As described above with reference to FIGS. 20 and 21, the petals 730 are configured to interface with the distal end portion 736 of the delivery capsule 712 (FIG. 24) and allow a prosthetic medical device (e.g., heart valve) to be loaded into the delivery capsule 712 without degrading or compressing the softer (lower durometer) distal end portion 736. In FIG. 24, the loader 810 is shown separated from a remainder of the loading assembly 800 and shows the free ends of the petals 730 extending radially inward and into the distal end portion 736 of the delivery capsule 712. Thus, the distal end portion 736 surrounds the free ends of the petals 730 and can more easily receive a radially compressed prosthetic medical device within the delivery capsule 712.

In some examples, free ends of the plurality of petals 730 can be unattached to one another and configured to flex. In other examples, the petals 730 can be continuous with one another, even at their free ends. In some examples, the petals 730 can comprise a relatively thin polymeric material. Thus, in some examples, the petals 730 can be softer and/or more flexible than a remainder of the loader 810.

Figures 25, 26:
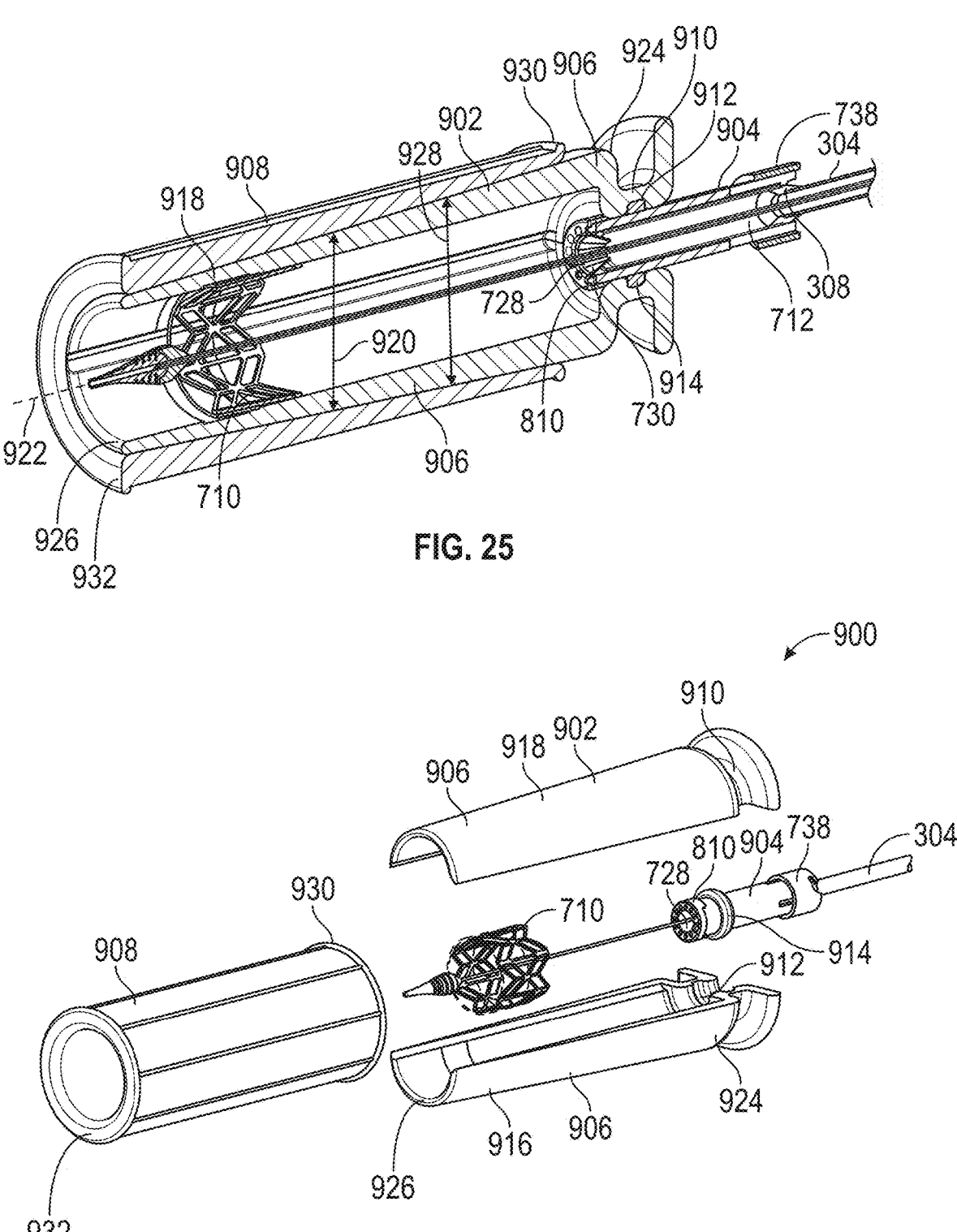
FIG. 25 is a perspective, cross-sectional view of another example of a loading assembly including a detachable device housing that is removable from a remainder of the loading assembly and comprises two separable shell portions configured to be held together around and to the remainder of the loading assembly with an annular sleeve.
FIG. 26 is an exploded view of the loading assembly of FIG. 25.

FIGS. 25 and 26 show another example of a loading assembly 900 including a detachable device housing 902 that is removable from (removably coupled to) a remainder of the loading assembly 900 (shown attached to the remainder of the loading assembly 900 in the cross-sectional view of FIG. 25 and removed from the remainder of the loading assembly 900 in the exploded view of FIG. 26). The device housing 902 comprises two separable shell portions (shells)

906. For example, each shell portion 906 can make up half of the device housing 902 and the shell portions 906 can be fully separable from one another a long a length (in the axial direction) of the device housing 902. The two separable shell portions 906 can be held together by an outer sleeve 908. The sleeve 908 can be configured as an annular member (tube) that is configured to slide onto, surround, and hold together the two shell portions 906 to form the device housing 902 (as shown in FIG. 25).

Each shell portion 906 can comprise a first (proximal end) portion 910 configured to couple with and around the loading capsule 904. For example, the first portion 910 can include a depression 912 that is configured to receive and couple around a collar portion (protrusion) 914 of the loading capsule 904. After coupling the first portions 910 of the two shell portions 906 around the loading capsule 904 and together, the sleeve 908 can be slid over outer surfaces 916 of second portions 918 of the shell portion 906 (each shell portion 906 comprising a second portion 918 that is continuous with the corresponding first portion 910) in order to hold the two shell portions 906 together and form the device housing 902.

In some examples, when the two shell portions 906 are arranged together (FIG. 25), an outer diameter 920 of the device housing 902 can decrease from proximal ends 924 of the second portions 918 of the shell portions 906 to distal ends 926 of the second portions 918 of the shell portions 906 (due to outer surfaces of the two shell portions 906 tapering radially inward relative to a central longitudinal axis 922 of the loading assembly 900). In a complementary manner, the sleeve 908 can have an inner diameter 928 (FIG. 25) that decreases from a proximal end 930 of the sleeve 908 to a distal end 932 of the sleeve 908.

In some examples, an inner diameter of the device housing 902 can also taper from the proximal ends 924 to the distal ends 926. The taper or decrease in diameter of the inner diameter of the device housing 902 can, in some examples, follow the taper of the outer diameter 920 of the device housing 902.

In some examples, a thickness (in the radial direction) of the sleeve 908 can be larger at its distal end 932 than its proximal end 930.

Figures 27, 28:
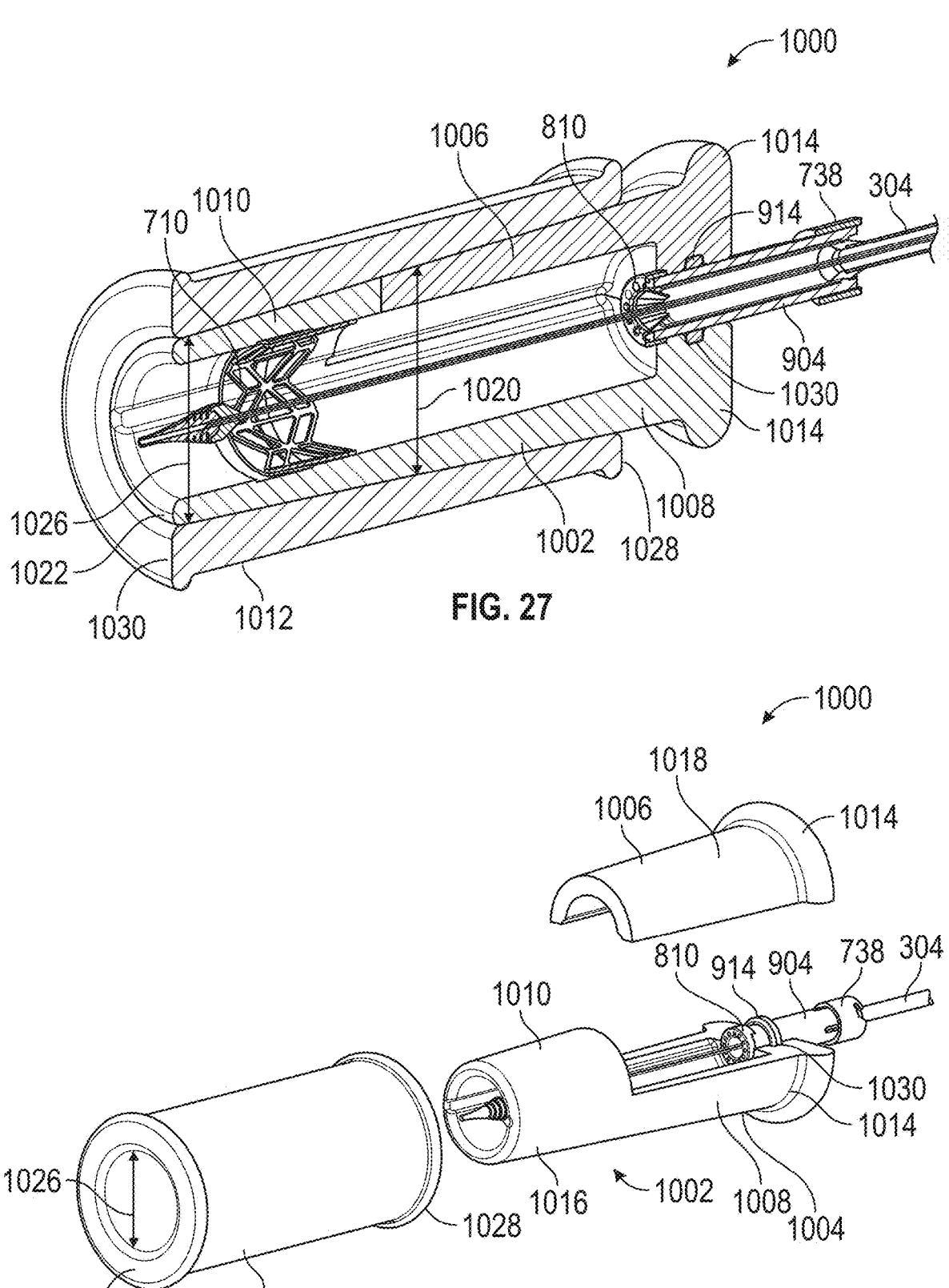
FIG. 27 is a perspective, cross-sectional view of another example of a loading assembly including a detachable device housing that is removable from a remainder of the loading assembly and comprises two separable shell portions configured to be held together around and to the remainder of the loading assembly with an annular sleeve, the two separable shell portions separable from one another along a portion of a length of the device housing.
FIG. 28 is an exploded view of the loading assembly of FIG. 27.

FIGS. 27 and 28 show another example of a loading assembly 1000 including a detachable device housing 1002 that is removable from (removably coupled to) a remainder of the loading assembly 1000 (shown attached to the remainder of the loading assembly 1000 in the cross-sectional view of FIG. 27 and removed from the remainder of the loading assembly 1000 in the exploded view of FIG. 28). The device housing 1002 can be similar to the device housing 902 of FIGS. 25 and 26, except instead of two separable full shell portions that each form one half of the device housing (shell portions 906 in FIGS. 25 and 26), the device housing 1002 comprises a first shell portion 1004 and a second shell portion 1006 where the second shell portion 1006 is a half shell portion that mates with a half shell portion 1008 of the first shell portion 1004 which also comprises a full annular portion 1010.

For example, the annular portion 1010 of the first shell portion 1004 can have a full (closed) circular cross-section and the half shell portion 1008 can have a semi (or half) circular cross-section. The annular portion 1010 and the half shell portion 1008 can be continuous with one and formed (e.g., molded) as one piece. In some examples, as shown in FIGS. 28 and 28, the annular portion 1010 forms a distal end portion of the first shell portion 1004 and the half shell portion 1008 can form a proximal end portion of the first shell portion 1004. The half shell portion 1008 is configured to mate with the second shell portion 1006 in order to form a full annular shell, thereby forming the device housing 1002 with the annular portion 1010 (as shown in FIG. 27). In this way, the first shell portion 1004 and the second shell portion 1006 of the device housing 1002 are only separable from one another along a portion of the total length (in the axial direction) of the device housing 1002.

The first shell portion 1004 and the second shell portion 1006 can be held together by an outer sleeve 1012. The sleeve 1012 can be configured as an annular member (tube) that is configured to slide onto, surround, and hold together the first shell portion 1004 and the second shell portion 1006 to form the device housing 1002 (as shown in FIG. 27).

The annular portion 1010 of the first shell portion 1004 can be sized and configured to surround and receive therein the prosthetic heart valve 710 (or another prosthetic medical device) (FIG. 27). Similar to the shell portions 906 of FIGS. 25 and 26, each of the second shell portion 1006 and the half shell portion 1008 of the first shell portion 1004 can comprise a first (proximal) end portion 1014 configured to couple with and around the loading capsule 904 (FIGS. 27 and 28). For example, the first end portion 1014 can include an annular cavity or depression 1030 that is configured to receive and couple around the collar portion 914 of the loading capsule 904.

After coupling the first end portions 1014 of the second shell portion 1006 and the half shell portion 1008 around the loading capsule 904 and together, the sleeve 1012 can be slid over an outer surface 1016 of the first shell portion 1004 and an outer surface 1018 of the second shell portion 1006 (FIG. 28), adjacent to or up to the first end portions 1014, in order to hold the first shell portion 1004 and second shell portion 1006 together and form the device housing 1002 (FIG. 27).

In some examples, when the first shell portion 1004 and second shell portion 1006 are arranged together (FIG. 27), an outer diameter 1020 of the device housing 1002 can decrease from the first end portions 1014 to a distal end 1022 of the device housing 1002. In a complementary manner, the sleeve 1012 can have an inner diameter 1026 (FIGS. 27 and 28) that decreases from a proximal end 1028 of the sleeve 1012 to a distal end 1030 of the sleeve 1012. In some examples, a thickness (in the radial direction) of the sleeve 1012 can be larger at its distal end 1030 than its proximal end 1028.

An exemplary method 1100 for securing a loading assembly to a distal end portion of a delivery apparatus and loading a prosthetic medical device (e.g., prosthetic heart valve) into a delivery capsule of the delivery apparatus using the loading assembly is shown in FIG. 29. The loading assembly described below with reference to FIG. 29 can be any one of the loading assemblies described herein with reference to FIGS. 3A-28. Further, in some examples, the prosthetic medical device can be a prosthetic heart valve, such as the prosthetic heart valve 200 shown in FIG. 2. In some examples, the delivery apparatus can be the delivery apparatus 100 shown in FIG. 1.

Method 1100 begins at 1102 and includes arranging a loading capsule of a loading assembly around a delivery capsule of a delivery apparatus, wherein the delivery apparatus optionally can be coupled to a distal end of a shaft of the delivery apparatus by a coupling (coupling member). For example, as shown in FIG. 12A (as described above) a loading capsule 316 can be arranged around (concentrically around) a delivery capsule 314 and the delivery capsule 314 can be coupled to a coupling 308 which is coupled to a distal end portion 306 of a shaft 304 (e.g., steerable or flexible shaft) of a delivery apparatus.

At 1104, the method includes moving a proximal end portion of the loading capsule comprising a plurality of axially extending flexible members (e.g., flexible members 326) into contact with the coupling (e.g., coupling 308) and flexing the flexible members radially outward as they slide along an outer surface of the coupling (e.g., as shown in FIG. 12A, as described above).

Method 1100 continues to 1106 which includes moving the flexible members radially inward and into engagement with one or more channels (e.g., channels 340 of coupling 308) depressed into the outer surface of the coupling, thereby coupling the loading capsule to the coupling (e.g., as shown in FIG. 12B, as described above). In some examples, one or more of the flexible members can comprise an inner protrusion extending from its inner surface (e.g., protrusion 338) which is configured to engage and mate with a corresponding channel of the coupling (as described above with reference to FIGS. 6-8 and 12B).

However, it may be possible for the flexible members to flex radially outward and disengage from the coupling, thereby uncoupling the loading assembly from the delivery apparatus. Thus, method 1100 continues to 1108 which includes sliding a collar (e.g., collar 318 of FIGS. 3A-8, collar 404 of FIGS. 13 and 14, or collar 504 of FIG. 15) of the loading assembly over the outer surface of the loading capsule, from a disengaged position to an engaged position where one or more locking features (or mating elements) of the collar engage one or more complementary locking features (or mating elements) on an outer surface of the flexible members and lock the flexible members in engagement with the coupling such that they cannot flex radially outward (thereby locking the loading assembly to the delivery apparatus, e.g., as shown in FIG. 12C). In one example, the one or more locking features of the collar can be the one or more slots 376 and the one or more complementary locking features on the outer surface of the flexible members can be the one or more outer protrusions 374 (as shown in FIGS. 4-8). In another example, the one or more locking features of the collar can be the helical groove 424 and the one or more complementary locking features on the outer surface of the flexible members can be the helical thread 410 (as shown in FIGS. 13 and 14). In another example, the one or more locking features of the collar can be the projection 518 and the one or more complementary locking features on the outer surface of the flexible members can be the slot 510 (as shown in FIG. 15).

In some examples, the method 1100 can optionally include, at 1110, attaching a device housing to a distal end portion of the loading assembly and arranging the prosthetic medical device, in a radially expanded or at least partially radially expanded configuration, within the device housing for storage and/or transport. As one example, the device housing 702 shown in FIGS. 18-20 can be secured to the distal end portion 706 of the loading capsule 704 (FIGS. 17-21). In some examples, the device housing 702 can be first positioned around the at least partially radially expanded prosthetic medical device (e.g., prosthetic heart valve 710 shown in FIGS. 17-21) and then screwed (or snapped or connected via another attachment interface) onto the loading capsule 704. In other examples, the device housing 702 can be first secured to the loading capsule 704 and then the prosthetic heart valve 710 can be inserted into the device housing 702 for storage and/or transport. As another example of the method at 1110, the device housing 802 shown in FIG. 22 can be secured to (e.g., screwed, snapped, or connected onto) the coupling element 806 which is coupled to the loading capsule 804. As another example of the method at 1110, the two shell portions 906 of the device housing 902 shown in FIGS. 25 and 26 can be assembled together and to the loading capsule 904, around the prosthetic medical device, and then the sleeve 908 can be slid over the two shell portions 906 to hold the device housing 902 together. As yet another example of the method at 1110, the second shell portion 1006 can be assembled to the half shell portion 1008 of the first shell portion 1004 of the device housing 1002 shown in FIGS. 27 and 28, around the prosthetic medical device and the distal end portion of the loading capsule 904, and then the sleeve 1012 can be slid over the first shell portion 1004 and the second shell portion 1006 to hold the device housing 1002 together.

In some examples, the method at 1100 can optionally further comprise inserting the device housing containing the prosthetic medical device (in an at least partially radially expanded state) and connected to the delivery apparatus into a sterile package (which can exclude a hydrating fluid) for shipping and storage prior to use at a hospital or other medical facility.

Method 1100 can continue to 1112 which includes loading a prosthetic medical device into the delivery capsule by at least partially radially compressing the prosthetic medical device and sliding it into and through a tapered loading member of the loading assembly that is coupled to a distal end portion of the loading capsule and further radially compressing (or maintaining in the radially compressed state) the prosthetic medical device as it slides through the loading member and into the delivery capsule. In some examples, the method at 1112 can include at least partially radially compressing the prosthetic medical device by sliding it through a tapered loader (e.g., tapered inner lumen of loader 320 of FIGS. 3A-3B) of the loading assembly and then further radially compressing the prosthetic medical device as it slides through a tapered portion extending proximally from a main portion of the loader (e.g., tapered portion 321 shown in FIGS. 12A-12C) and into the delivery capsule.

Figure 30:
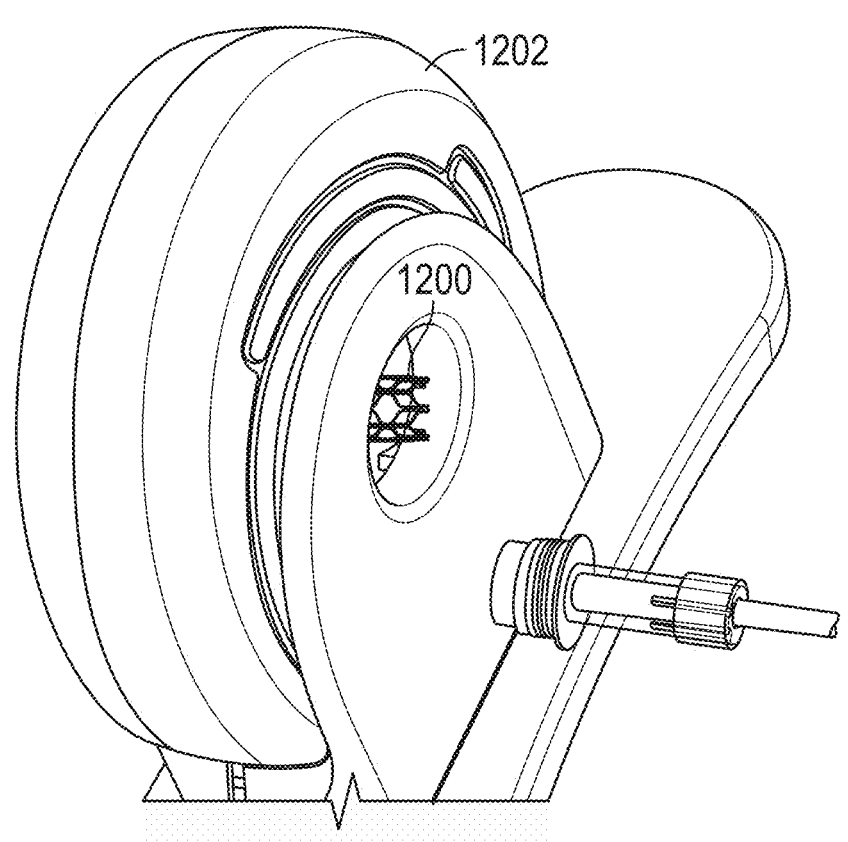
FIG. 30 is a perspective view of an exemplary crimping device for crimping a prosthetic medical device into a radially compressed configuration.
Figure 31:
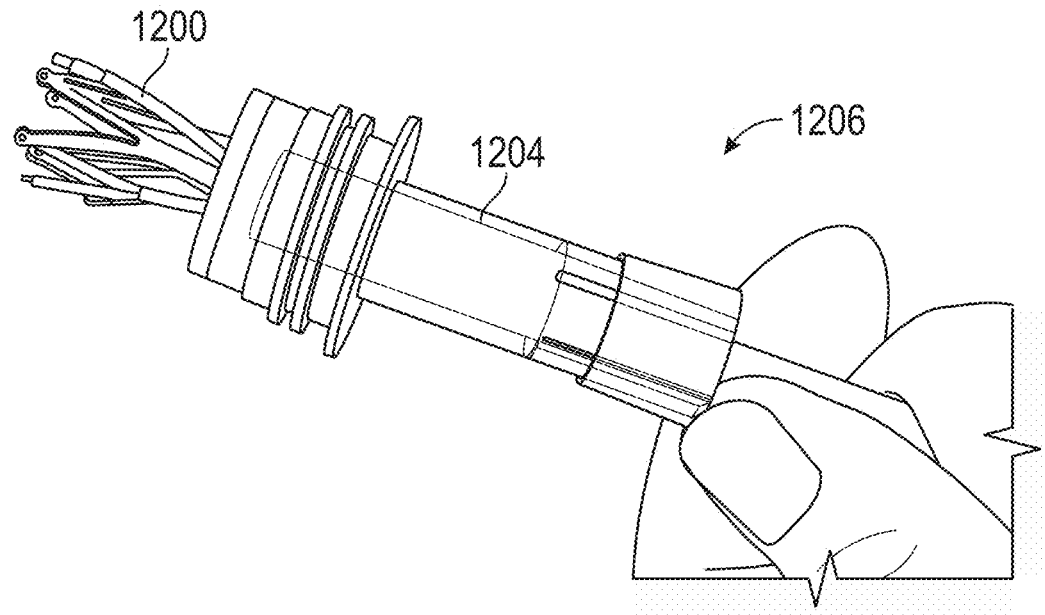
FIG. 31 is a perspective view of a radially compressed prosthetic medical device being loaded into an exemplary loading assembly.

In some examples, in lieu of or in addition to using a loader 320, at least partially radially compressing the prosthetic medical device at 1112 can include inserting the prosthetic medical device 1200 into a crimping device 1202 and radially compressing the prosthetic medical device 1200 with the crimping device, as shown in FIG. 30. In some examples, the method at 1112 can further include pulling or pushing the at least partially radially compressed prosthetic medical device 1200 into the loading capsule 1204 (which surrounds the delivery capsule) of the loading assembly 1206, as shown in FIG. 31, and through a tapered loader or loading element attached to the loading capsule and extending into the delivery capsule (e.g., loader 726 of FIGS. 17-21 or loader 810 of FIGS. 22-28), thereby loading the radially compressed prosthetic medical device 1200 into the delivery capsule of the delivery apparatus which is surrounded by and connected to the loading capsule 1204 (as described herein).

In this way, the loading assemblies and related methods described herein can be configured to create a more secure attachment between a loading assembly and a distal end portion of a delivery apparatus, thereby allowing a prosthetic medical device (such as a prosthetic heart valve) to be more easily loaded into a delivery capsule of the delivery apparatus, without compressing or causing degradation of a flexible shaft of the delivery apparatus (e.g., a steerable, flexible shaft that is coupled to the delivery capsule via a coupling).

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A medical system comprising: a delivery apparatus for implanting a prosthetic medical device in a patient's body, the delivery apparatus comprising: a flexible shaft; a coupling attached to a distal end of the flexible shaft; and a delivery capsule coupled to the coupling and extending distally from the coupling, away from the distal end of the flexible shaft; and a loading assembly comprising: a loading capsule comprising a plurality of axially extending flexible members configured to couple to an outer surface of the coupling and flex radially outward; and a collar disposed around the loading capsule and configured to lock the plurality of flexible members in engagement with the coupling such that the plurality of flexible members cannot flex radially outward.

Example 2. The system of any example herein, particularly example 1, wherein the loading assembly further comprises a loader coupled to a distal end portion of the loading capsule and comprising a tapered portion configured to extend into a distal end portion of the delivery capsule when the loading capsule is arranged around the delivery capsule and coupled to the coupling.

Example 3. The system of any example herein, particularly example 2, wherein the tapered portion comprises a plurality of wedge-shaped petals having free ends that extend into the distal end portion of the delivery capsule and wherein the distal end portion of the delivery capsule surrounds an outer surface of the plurality of petals.

Example 4. The system of any example herein, particularly example 2 or example 3, further comprising a radially expandable and compressible prosthetic heart valve and wherein the loader is configured to load the prosthetic heart valve, in an at least partially radially compressed state, into the delivery capsule while the loading capsule is coupled to the coupling.

Example 5. The system of any example herein, particularly any one of examples 1-4, wherein the coupling comprises a hard, plastic material, wherein the distal end of the flexible shaft comprises a flexible material, and wherein the flexible shaft is steerable and has an adjustable curvature.

Example 6. The system of any example herein, particularly any one of examples 1-5, wherein the coupling comprises a first portion coupled to the delivery capsule, a second portion comprising one or more channels depressed, in a radial direction, into the outer surface of the coupling, and a third portion coupled to the distal end of the flexible shaft, wherein the second portion is disposed between the first portion and the third portion, and wherein the one or more channels are configured to receive one or more inner protrusions extending radially inward from inner surfaces of the plurality of flexible members.

Example 7. The system of any example herein, particularly example 6, wherein each flexible member of the plurality of flexible members comprises a free end portion with an inner protrusion extending radially inward from an inner surface of the flexible member, the inner protrusion configured to be received within and couple to a corresponding channel of the one or more channels of the coupling.

Example 8. The system of any example herein, particularly any one of examples 1-7, wherein the collar is disposed around and configured to slide along an outer surface of the loading capsule and wherein an inner surface of the collar comprises a first mating element configured to mate with and couple to a complementary second mating element on an outer surface of one or more of the plurality of flexible members such that plurality of flexible members are locked in engagement with the coupling.

Example 9. The system of any example herein, particularly example 8, wherein the first mating element is a slot and the second mating element is an outer protrusion, the outer protrusion configured to slide into and along the slot as the collar rotates and be held within a closed end of the slot by one or more retaining features of the slot.

Example 10. The system of any example herein, particularly example 8, wherein the first mating element is a helical groove depressed into the inner surface of the collar and the second mating element is a helical thread, the helical groove configured to slide along and thread onto the helical thread.

Example 11. The system of any example herein, particularly example 8, wherein the first mating element is a projection extending from the inner surface of the collar and the second mating element is a slot in the outer surface of one flexible member of the plurality of flexible members, the projection configured to extend into and couple with the slot.

Example 12. The system of any example herein, particularly any one of examples 1-11, wherein the loading assembly further comprises a device housing removably coupled to the loading capsule, the device housing having an inner cavity configured to receive and store a prosthetic medical device in an at least partially radially expanded state.

Example 13. The system of any example herein, particularly example 12, wherein the device housing comprises a proximal end portion including a first attachment interface and the loading assembly comprises a second attachment interface included on or attached to a distal end portion of the loading capsule, the first attachment interface and the second attachment interface configured to removably couple to one another, and wherein a distal end portion of the device housing comprises the inner cavity.

Example 14. A medical assembly comprising: a coupling configured to connect a delivery capsule to a distal end of a shaft of a delivery apparatus, wherein the coupling includes one or more channels depressed into an outer surface of the coupling; a loading capsule configured to be coupled to the coupling, wherein the loading capsule has a proximal end portion comprising a plurality of axially extending flexible members spaced apart from one another around a circumference of the proximal end portion that are configured to flex in a radial direction and couple with the one or more channels of the coupling member; and a collar disposed around the loading capsule and configured to slide along the loading capsule and couple to the plurality of flexible members and hold the plurality of flexible members in engagement with the one or more channels of the coupling.

Example 15. The assembly of any example herein, particularly example 14, wherein the loading capsule further includes an annular distal end portion and wherein the plurality of flexible members are configured to flex radially outward from the distal end portion, relative to a central longitudinal axis of the assembly.

Example 16. The assembly of any example herein, particularly example 14 or example 15, further comprising a loader coupled to a distal end of the loading capsule and comprising a tapered portion that tapers radially inward, in a proximal direction toward the proximal end portion of the loading capsule.

Example 17. The assembly of any example herein, particularly example 16, wherein the tapered portion comprises a plurality of wedge-shaped petals that taper radially inward and wherein free ends of the plurality of petals are configured to extend into the delivery capsule such that a distal end portion of the delivery capsule surround the plurality of petals.

Example 18. The assembly of any example herein, particularly any one of examples 14-17, wherein one or more flexible members of the plurality of flexible members includes an inner protrusion extending radially inward from an inner surface of the one or more flexible members that is configured to engage with a corresponding channel of the one or more channels of the coupling.

Example 19. The assembly of any example herein, particularly any one of examples 14-17, wherein each flexible member of the plurality of flexible members includes an inner protrusion extending radially inward from an inner surface of the flexible member that is configured to engage with a corresponding channel of the one or more channels of the coupling.

Example 20. The assembly of any example herein, particularly example 19, wherein the one or more channels of the coupling comprises a plurality of discrete channels spaced apart from one another around a circumference of the coupling and wherein each channel is configured to couple with the inner protrusion of a corresponding one of the plurality of flexible members.

Example 21. The assembly of any example herein, particularly any one of examples 14-20, wherein the collar includes a slot and the loading capsule includes an outer protrusion extending radially outward from an outer surface of one of the plurality of flexible members, the outer protrusion configured to couple with the slot such that the collar locks the plurality of flexible members in engagement with the one or more channels of the coupling.

Example 22. The assembly of any example herein, particularly example 21, wherein the slot includes a cantilevered extension portion with a retaining element configured to hold the outer protrusion within a closed end of the slot.

Example 23. The assembly of any example herein, particularly any one of examples 14-20, wherein the collar includes a helical groove in an inner surface of the collar and wherein the plurality of flexible members includes a helical thread extending across an outer surface of the plurality of flexible members that is configured to engage with the helical groove to lock the collar in engagement with the plurality of flexible members and hold the plurality of flexible members in engagement with the one or more channels of the coupling.

Example 24. The assembly of any example herein, particularly any one of examples 14-20, wherein one flexible member of the plurality of flexible members comprises a slot extending into an outer surface of the flexible member and wherein the collar comprises a mating projection extending from an inner surface of the collar and configured to engage the slot to lock the collar in engagement with the plurality of flexible members and hold the plurality of flexible members in engagement with the one or more channels of the coupling.

Example 25. The assembly of any example herein, particularly example 23 or example 24, wherein free ends of the plurality of flexible members can comprise a radial extension portion that extends radially outward from the outer surface of the plurality of flexible members such that the collar is stopped from moving further in an axial direction, past the radial extension portion.

Example 26. The assembly of any example herein, particularly any one of examples 14-25, wherein the coupling comprises a first portion configured to receive the delivery capsule around an outer surface of the first portion, a second portion comprising the one or more channels, and a third portion configured to receive the distal end of the shaft, the second portion disposed between the first portion and third portion.

Example 27. The assembly of any example herein, particularly any one of examples 14-26, further comprising a device housing removably coupled to a distal end portion of the loading capsule and that extends distally from the distal end portion of the loading capsule when coupled to the loading capsule, the device housing configured to receive therein and surround a prosthetic medical device in an at least partially radially expanded configuration.

Example 28. The assembly of any example herein, particularly example 27, wherein a proximal end portion of the device housing comprises an attachment interface configured to be removably coupled to a complementary attachment interface on the distal end portion of the loading capsule.

Example 29. The assembly of any example herein, particularly example 28, wherein the attachment interface of the device housing comprises a plurality of threads and the complementary attachment interface of the loading capsule comprises a plurality of complementary threads.

Example 30. The assembly of any example herein, particularly example 27, further comprising a coupling element comprising a first attachment interface, the coupling element coupled to the distal end portion of the loading capsule and wherein a proximal end portion of the device housing comprises a second attachment interface configured to be removably coupled to the first attachment interface.

Example 31. The assembly of any example herein, particularly example 27, wherein the device housing comprises a first shell portion and a second shell portion that are separable from one another and configured to couple together around and to the distal end portion of the loading capsule and further comprising an annular sleeve configured to slide onto, surround, and hold together the first shell portion and the second shell portion to form the device housing.

Example 32. The assembly of any example herein, particularly example 31, wherein the first shell portion and the second shell portion are each half shell portions that each make up half the device housing and wherein the first shell portion and the second shell portion are fully separable from one another along an entire length of the device housing.

Example 33. The assembly of any example herein, particularly example 31, wherein the first shell portion comprises a full annular portion and a half shell portion and wherein the second shell portion is a half shell portion that is configured to mate with the half shell portion of the first shell portion, the first shell portion and the second shell portion only separable from one another along a portion of an entire length of the device housing.

Example 34. A loading assembly for loading a radially expandable and compressible prosthetic medical device into a delivery apparatus, the assembly comprising: a loading capsule having a proximal end portion comprising a plurality of axially extending flexible members spaced apart from one another around a circumference of the proximal end portion that are configured to flex in a radial direction and couple with a distal end portion of the delivery apparatus, wherein a radially outward facing surface of one or more flexible members of the plurality of flexible members includes a first mating element; and a collar disposed around the loading capsule and configured to slide along the loading capsule, the collar comprising a second mating element configured to mate with and couple to the first mating element to prevent the plurality of flexible members from flexing radially outward.

Example 35. The assembly of any example herein, particularly example 34, wherein the loading capsule further includes an annular distal end portion and wherein the plurality of flexible members are configured to flex radially outward from the distal end portion, relative to a central longitudinal axis of the assembly.

Example 36. The assembly of any example herein, particularly example 34, wherein the second mating element of the collar is disposed on a radially inward facing surface of the collar.

Example 37. The assembly of any example herein, particularly example 35 or example 36, wherein the second mating element is a slot and the first mating element is an outer protrusion, the outer protrusion configured to slide into and along the slot as the collar rotates and be held within a closed end of the slot by one or more retaining features of the slot.

Example 38. The assembly of any example herein, particularly example 35 or example 36, wherein the second mating element is a helical groove depressed into a radially inward facing surface of the collar and the first mating element is a helical thread, the helical groove configured to slide along and thread onto the helical thread.

Example 39. The assembly of any example herein, particularly example 35 or example 36, wherein the second mating element is a projection extending from a radially inward facing surface of the collar and the first mating element is a slot in the radially outward facing surface of the one or more flexible members, the projection configured to extend into and couple with the slot.

Example 40. The assembly of any example herein, particularly any one of examples 34-39, further comprising a loader coupled to a distal end of the loading capsule and comprising a tapered portion that tapers radially inward, in a proximal direction toward the proximal end portion of the loading capsule.

Example 41. The assembly of any example herein, particularly example 40, wherein the tapered portion comprises a plurality of wedge-shaped petals that taper radially inward.

Example 42. The assembly of any example herein, particularly any one of examples 34-41, wherein each flexible member of the plurality of flexible members includes an inner protrusion extending radially inward from a radially inward facing surface of the flexible member.

Example 43. The assembly of any example herein, particularly example 42, further comprising a delivery apparatus comprising a shaft and a coupling mounted to a distal end portion of the shaft and wherein the inner protrusion of each flexible member is configured to engage with a corresponding channel depressed into a radially outward facing surface of the coupling.

Example 44. The assembly of any example herein, particularly example 43, wherein the delivery apparatus further comprises a delivery capsule coupled to the coupling and wherein when the loading capsule is coupled to the coupling, the loading capsule is disposed around the delivery capsule.

Example 45. The assembly of any example herein, particularly any one of examples 34-44, further comprising a device housing removably coupled to a distal end portion of the loading capsule and that extends distally from the distal end portion of the loading capsule when coupled to the loading capsule, the device housing configured to receive therein and surround a prosthetic medical device in an at least partially radially expanded configuration.

Example 46. A method comprising: moving a proximal end portion of a loading capsule of a loading assembly, the loading capsule comprising a plurality of axially extending flexible members, into contact with a coupling of a delivery apparatus and flexing the plurality of flexible members radially outward as a radially extending inner protrusion of each flexible member of the plurality of flexible members slides along an outer surface of the coupling, the coupling connecting a delivery capsule of the delivery apparatus to a distal end portion of a shaft of the delivery apparatus; and moving the plurality of flexible members radially inward such that the inner protrusion of each flexible member is engaged with one or more channels depressed into the outer surface of the coupling, thereby coupling the loading capsule to the coupling with the loading capsule surrounding the delivery capsule.

Example 47. The method of any example herein, particularly example 46, further comprising sliding a collar of the loading assembly over an outer surface of the loading capsule, from a disengaged position to an engaged position where one or more locking features of the collar engage one or more complementary locking features on an outer surface of the plurality of flexible members and lock the plurality of flexible members in engagement with the coupling such that they cannot flex radially outward.

Example 48. The method of any example herein, particularly example 47, wherein sliding the collar over the outer surface of the loading capsule from the disengaged position to the engaged position includes sliding the collar over the outer surface of the loading capsule until the one or more locking features of the collar contact the one or more complementary locking features of the plurality of flexible member and then rotating the collar to engage the one or more locking features of the collar and the one or more complementary locking features of the plurality of flexible members and move the collar into the engaged position.

Example 49. The method of any example herein, particularly example 47 or example 48, wherein the one or more locking features of the collar include one or more slots and the one or more complementary locking features on the outer surface of the plurality of flexible members include one or more outer protrusions extending radially outward from one or more flexible members of the plurality of flexible members.

Example 50. The method of any example herein, particularly example 47 or example 48, wherein the one or more locking features of the collar include a helical groove and the one or more complementary locking features on the outer surface of the flexible members include a helical thread.

Example 51. The method of any example herein, particularly example 47, wherein the one or more locking features of the collar include one or more projections and the one or more complementary locking features on the outer surface of the flexible members include one or more slots extending into the outer surface of one or more flexible members of the plurality of flexible members.

Example 52. The method of any example herein, particularly any one of examples 46-51, further comprising loading a prosthetic medical device into the delivery capsule by at least partially radially compressing the prosthetic medical device and sliding it into and through a tapered loading member of the loading assembly that is coupled to a distal end portion of the loading capsule, and further radially compressing or the prosthetic medical device as it slides through the loading member and into the delivery capsule.

Example 53. The method of any example herein, particularly example 52, wherein the loading member comprises a tapered portion comprising a plurality of wedge-shaped petals that taper radially inward to free ends of the plurality of petals that extend into an interior of a distal end portion of the delivery capsule.

Example 54. The method of any example herein, particularly example 52 or example 53, wherein the prosthetic medical device is a radially expandable and compressible prosthetic heart valve.

Example 55. The method of any example herein, particularly any one of examples 46-51, further comprising attaching a device housing to a distal end portion of the loading assembly and arranging a prosthetic medical device, in a radially expanded or at least partially radially expanded configuration, within the device housing, the device housing removably coupled to the distal end portion of the loading assembly.

Example 56. The method of any example herein, particularly example 55, wherein attaching the device housing to the distal end portion of the loading assembly includes attaching the device housing to the distal end portion of the loading capsule by coupling one or more interlocking features on an attachment interface of the device housing to one or more complementary interlocking features on an attachment interface of the distal end portion of the loading capsule and wherein the one or more interlocking feature and the one or more complementary interlocking features are detachable from one another.

Example 57. The method of any example herein, particularly example 55, wherein attaching the device housing to the distal end portion of the loading assembly includes attaching the device housing to a coupling element that is coupled to the loading capsule by coupling one or more interlocking features on an attachment interface of the device housing to one or more complementary interlocking features on an attachment interface of the coupling element and wherein the one or more interlocking feature and the one or more complementary interlocking features are detachable from one another.

Example 58. The method of any example herein, particularly example 55, wherein the device housing comprises two shell portions that are separable from one another along a length of the device housing and wherein attaching the device housing to the distal end portion of the loading assembly includes assembling the two shell portions together and to the loading capsule, around the prosthetic medical device, and then sliding a sleeve over and around the two shell portions to hold the device housing together.

Example 59. The method of any example herein, particularly example 55, wherein the device housing comprises a first shell portion and a second shell portion, the first shell portion including a half shell portion that is separable from the second shell portion, the second shell portion extending along a portion of a length of the device housing, and wherein attaching the device housing to the distal end portion of the loading assembly includes assembling the second shell portion to the half shell portion of the first shell portion together and to the loading capsule, around the prosthetic medical device, and then sliding a sleeve over and around the first shell portion and the second shell portion to hold the device housing together.

Example 60. The method of any example herein, particularly any one of examples 55-59, further comprising inserting the device housing containing the prosthetic medical device and connected to the loading assembly, which is connected to the delivery apparatus, into a sterile package.

Example 61. The method of any example herein, particularly any one of examples 55-59, further comprising removing the device housing from the distal end portion of the loading assembly to expose the prosthetic medical device and loading the prosthetic medical device into the delivery capsule by at least partially radially compressing the prosthetic medical device and sliding it into and through a tapered loading member of the loading assembly that is coupled to a distal end portion of the loading capsule and into the delivery capsule.

Example 62. The method of any example herein, particularly any one of examples 46-61, wherein the flexible members of the plurality of flexible members are spaced apart from one another around a circumference of the proximal end portion of the loading capsule, wherein the inner protrusion of each flexible member extends radially inward from an inner surface of the flexible member, toward a central longitudinal axis of the loading assembly, and wherein the one or more channels of the coupling includes a plurality of discrete channels spaced apart from one another around a circumference of the coupling, each channel of the plurality of channels configured to receive the inner protrusion of a corresponding flexible member of the plurality of flexible members.

Example 63. A loading assembly for loading a radially expandable and compressible prosthetic medical device into a delivery apparatus, the assembly comprising: a loading capsule comprising an annular distal end portion and a proximal end portion configured to be coupled to the delivery apparatus; a loader coupled to the distal end portion of the loading capsule and comprising a tapered portion extending proximally into an interior of the distal end portion of the loading capsule; and a device housing removably coupled to the loading capsule, the device housing extending distally from the distal end portion of the loading capsule, and the device housing comprising an inner cavity configured to receive the prosthetic medical device in an at least partially radially expanded state.

Example 64. The loading assembly of any example herein, particularly example 63, wherein a proximal end portion of an inner surface of the device housing comprises a first attachment interface having one or more interlocking features configured to removably couple to one or more complementary interlocking features of a second attachment interface disposed on or coupled to the distal end portion of the loading capsule.

Example 65. The loading assembly of any example herein, particularly example 64, wherein the second attachment interface is disposed on the distal end portion of the loading capsule, the distal end portion having a larger diameter than the proximal end portion of the loading capsule.

Example 66. The loading assembly of any example herein, particularly example 64, wherein the second attachment interface is disposed on a coupling element that is attached to the distal end portion of the loading capsule.

Example 67. The loading assembly of any example herein, particularly any one of examples 64-66, wherein the first and second attachment interfaces comprise threads.

Example 68. The loading assembly of any example herein, particularly example 63, wherein the device housing comprises a first shell portion and a second shell portion that are separable from one another and configured to be held together around and to the distal end portion of the loading capsule by an annular sleeve when the annular sleeve is arranged around the first shell portion and the second shell portion.

Example 69. The loading assembly of any example herein, particularly example 68, where the first shell portion and the second shell portion are each half shell portions that are separable from one another along an entire length the device housing.

Example 70. The loading assembly of any example herein, particularly example 68, wherein the first shell portion comprises a full annular portion and a half shell portion and the second shell portion is a half shell portion configured to mate with the half shell portion of the first shell portion.

Example 71. The loading assembly of any example herein, particularly any one of examples 63-70, wherein the proximal end portion of the loading capsule comprises a plurality of flexible members spaced apart from one another around a circumference of the proximal end portion, each flexible member comprising a free end portion including an inner protrusion extending radially inward from an inner surface of the flexible member that is configured to engage with a coupling of the delivery apparatus such that the loading capsule is coupled to the delivery apparatus.

Example 72. The loading assembly of any example herein, particularly example 71, further comprising a collar disposed around the loading capsule and including a first mating element on an inner surface of the collar, the first mating element configured to mate with and couple to a complementary second mating element on an outer surface of one or more of the plurality of flexible members such that plurality of flexible members are locked in engagement with the coupling.

Example 73. The loading assembly of any example herein, particularly any one of examples 63-72, wherein the prosthetic medical device is a prosthetic heart valve comprising a radially expandable and compressible frame with a plurality of leaflets attached to the frame.

Example 74. A medical assembly comprising: a delivery apparatus comprising a delivery capsule, a flexible shaft, and a rigid coupling that connects the delivery capsule to the flexible shaft; a loading assembly comprising a loading capsule coupled to the coupling and a device housing removably coupled to the loading capsule and extending distally from the loading capsule; a radially expandable and compressible prosthetic heart valve disposed within and surrounded by the device housing, the prosthetic heart valve in an at least partially radially expanded configuration; and a sterile package containing the delivery apparatus, the loading assembly, and the prosthetic heart valve.

Example 75. The medical assembly of any example herein, particularly example 74, wherein the prosthetic heart valve comprises a radially expandable and compressible frame and a plurality of dry tissue leaflets attached to the frame and wherein the sterile package is free of liquid.

Example 76. The medical assembly of any example herein, particularly example 74 or example 75, wherein a proximal end portion of an inner surface of the device housing comprises a first attachment interface having one or more interlocking features configured to removably couple to one or more complementary interlocking features of a second attachment interface disposed on or coupled to a distal end portion of the loading capsule.

Example 77. The medical assembly of any example herein, particularly any one of examples 74-76, wherein a proximal end portion of the loading capsule comprises a plurality of flexible members that are spaced apart from one another around a circumference of the proximal end portion, each flexible member of the plurality of flexible members configured to flex radially outward and comprising an inner protrusion configured to couple to a channel depressed into an outer surface of the coupling.

Example 78. The medical assembly of any example herein, particularly example 77, further comprising a collar disposed around the loading capsule and including a first mating element on an inner surface of the collar, the first mating element configured to mate with and couple to a complementary second mating element on an outer surface of one or more of the plurality of flexible members such that plurality of flexible members are locked in engagement with the coupling.

In view of the many possible examples to which the principles of the disclosed technology may be applied, it should be recognized that the illustrated examples are only preferred examples of the disclosed technology and should not be taken as limiting the scope of the claimed subject matter. Rather, the scope of the claimed subject matter is defined by the following claims and their equivalents.

We claim:

1. A medical system comprising:
   a delivery apparatus for implanting a prosthetic medical device in a patient's body, the delivery apparatus comprising:
   a flexible shaft;
   a coupling attached to a distal end of the flexible shaft; and
   a delivery capsule coupled to the coupling and extending distally from the coupling, away from the distal end of the flexible shaft; and
   a loading assembly comprising:
   a loading capsule comprising a plurality of axially extending flexible members configured to couple to an outer surface of the coupling and flex radially outward; and
   a collar disposed around the loading capsule and configured to lock the plurality of flexible members in engagement with the coupling such that the plurality of flexible members cannot flex radially outward.

2. The medical system of claim 1, wherein the loading assembly further comprises a loader coupled to a distal end portion of the loading capsule and comprising a tapered portion configured to extend into a distal end portion of the delivery capsule when the loading capsule is arranged around the delivery capsule and coupled to the coupling.

3. The medical system of claim 2, wherein the tapered portion comprises a plurality of wedge-shaped petals having free ends that extend into the distal end portion of the delivery capsule and wherein the distal end portion of the delivery capsule surrounds an outer surface of the plurality of petals.

4. The medical system of claim 2, further comprising a radially expandable and compressible prosthetic heart valve, and wherein the loader is configured to load the prosthetic heart valve, in an at least partially radially compressed state, into the delivery capsule while the loading capsule is coupled to the coupling.

5. The medical system of claim 1, wherein the coupling comprises a hard, plastic material, wherein the distal end of the flexible shaft comprises a flexible material, and wherein the flexible shaft is steerable and has an adjustable curvature.

6. The medical system of claim 1, wherein the coupling comprises a first portion coupled to the delivery capsule, a second portion comprising one or more channels depressed, in a radial direction, into the outer surface of the coupling, and a third portion coupled to the distal end of the flexible shaft, wherein the second portion is disposed between the first portion and the third portion, and wherein the one or more channels are configured to receive one or more inner protrusions extending radially inward from inner surfaces of the plurality of flexible members.

7. The medical system of claim 6, wherein each flexible member of the plurality of flexible members comprises a free end portion with an inner protrusion extending radially inward from an inner surface of the flexible member, the inner protrusion configured to be received within and couple to a corresponding channel of the one or more channels of the coupling.

8. The medical system of claim 1, wherein the collar is disposed around and configured to slide along an outer surface of the loading capsule, and wherein an inner surface of the collar comprises a first mating element configured to mate with and couple to a complementary second mating element on an outer surface of one or more of the plurality of flexible members such that plurality of flexible members are locked in engagement with the coupling.

9. The medical system of claim 1, wherein the loading assembly further comprises a device housing removably coupled to the loading capsule, the device housing having an inner cavity configured to receive and store a prosthetic medical device in an at least partially radially expanded state.

10. The medical system of claim 9, wherein the device housing comprises a proximal end portion including a first attachment interface and the loading assembly comprises a second attachment interface included on or attached to a distal end portion of the loading capsule, the first attachment interface and the second attachment interface configured to removably couple to one another, and wherein a distal end portion of the device housing comprises the inner cavity.

\* \* \* \* \*